(12) United States Patent
Sharkey et al.

(10) Patent No.: US 6,379,350 B1
(45) Date of Patent: Apr. 30, 2002

(54) SURGICAL INSTRUMENT FOR ABLATION AND ASPIRATION

(75) Inventors: Hugh R. Sharkey, Woodside; Bruno Strul, Portola Valley; Daren L. Stewart, Belmont; John Ashley, San Francisco; Ramiro L. Reyes, Union City, all of CA (US)

(73) Assignee: Oratec Interventions, Inc., Menlo Park, CA (US)

(*) Notice: Subject to any disclaimer, the term of this patent is extended or adjusted under 35 U.S.C. 154(b) by 0 days.

(21) Appl. No.: 09/412,878

(22) Filed: Oct. 5, 1999

(51) Int. Cl.[7] .............................................. A61B 18/18
(52) U.S. Cl. .............................. 606/41; 606/48; 606/49; 606/50
(58) Field of Search .............................. 4/21; 6/41–50; 7/101

(56) References Cited

U.S. PATENT DOCUMENTS

| | | |
|---|---|---|
| 164,184 A | 8/1875 | Kidder |
| 300,155 A | 6/1884 | Starr |
| 371,664 A | 10/1887 | Brannan et al. |
| 452,220 A | 5/1891 | Gunning |
| 1,314,855 A | 9/1919 | Carpenter |
| 1,366,756 A | 1/1921 | Wappler |
| 1,731,627 A | 10/1929 | Johnson et al. |
| 1,735,271 A | 12/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 11/1934 | Kimble |
| 2,002,594 A | 5/1935 | Wappler et al. |
| 2,004,559 A | 6/1935 | Wappler et al. |
| 2,050,904 A | 8/1936 | Trice |
| 2,056,377 A | 10/1936 | Wappler |
| 2,224,464 A | 12/1940 | Wolf |
| 2,275,167 A | 3/1942 | Bierman |

(List continued on next page.)

FOREIGN PATENT DOCUMENTS

GB    2160102 A    12/1985

OTHER PUBLICATIONS

Lee Beadling, Bi–Polar electrosurgical devices: Sculpting the future of arthroscopy, Orthopedics Today, Jan. 1997, vol. 17, No. 1, SLACK, Inc., Medical Publisher.

*Primary Examiner*—Linda C. M. Dvorak
*Assistant Examiner*—David M. Ruddy
(74) *Attorney, Agent, or Firm*—Flehr Hohbach Test Albritton & Herbert LLP

(57) ABSTRACT

An electrosurgical aspiration instrument that permits aspiration of an area being treated by the instrument. The instrument is coupled at a proximal end to a power source and includes an energy application surface area at a distal end. The power source supplied energy to the energy application surface area such that the distal end of the instrument may apply energy to the treatment area to modify the characteristics of biological material, such as biological tissue in the area. An aspiration lumen is formed through the instrument with an opening through the energy application surface area. The energy application surface area is configured to reduce blockage of the opening. Accordingly, aspiration may be performed simultaneously with electrosurgical treatment whereby unwanted matter such as by-products, biological debris and excess fluid is removed from the treatment area. The electrosurgical aspiration instrument also permits both functions to be performed at different times, with the advantage of not requiring instruments to be switched on during the treatment procedure or removed from the treatment site.

11 Claims, 12 Drawing Sheets

U.S. PATENT DOCUMENTS

| | | | | |
|---|---|---|---|---|
| 2,888,928 | A | 6/1959 | Seiger | |
| 3,152,590 | A | 10/1964 | Zurdo et al. | |
| 3,163,165 | A | 12/1964 | Isakawa | |
| 3,460,539 | A | 8/1969 | Anhalt, Sr. | |
| 3,595,239 | A | 7/1971 | Petersen | |
| 3,768,482 | A | 10/1973 | Shaw | |
| 3,828,780 | A | 8/1974 | Morrison, Jr. | 128/275.1 |
| 3,870,047 | A | 3/1975 | Gonser | |
| 3,901,242 | A | 8/1975 | Storz | |
| 3,902,494 | A | 9/1975 | Haberlin | |
| 3,920,021 | A | 11/1975 | Hiltebrandt | |
| 3,920,022 | A | 11/1975 | Pastor | |
| 3,938,527 | A | 2/1976 | Rioux et al. | |
| 3,987,795 | A | 10/1976 | Morrison | |
| 4,033,351 | A | 7/1977 | Hetzel | 128/303.14 |
| 4,043,342 | A | 8/1977 | Morrison, Jr. | 128/303.14 |
| 4,202,337 | A | 5/1980 | Hren et al. | 128/303.14 |
| 4,228,800 | A | 10/1980 | Degler, Jr. et al. | 128/303.14 |
| 4,347,842 | A | 9/1982 | Beale | 128/276 |
| 4,381,007 | A | 4/1983 | Doss | 128/303.1 |
| 4,476,862 | A | 10/1984 | Pao | 128/303.17 |
| 4,483,338 | A | 11/1984 | Bloom et al. | 128/303.13 |
| 4,532,924 | A | 8/1985 | Auth et al. | 128/303.17 |
| 4,593,691 | A | 6/1986 | Lindstrom et al. | 128/303.14 |
| 4,682,596 | A | 7/1987 | Bales et al. | 128/303.14 |
| 4,765,331 | A | 8/1988 | Petruzzi et al. | 128/303.14 |
| 4,927,420 | A | 5/1990 | Newkirk et al. | |
| 5,009,656 | A | 4/1991 | Reimels | 606/48 |
| 5,083,565 | A | 1/1992 | Parins | 128/642 |
| 5,098,431 | A | 3/1992 | Rydell | 606/48 |
| RE33,925 | E | 5/1992 | Bales et al. | 606/48 |
| 5,125,928 | A | 6/1992 | Parins et al. | 606/48 |
| 5,195,959 | A | 3/1993 | Smith | 604/34 |
| 5,217,459 | A | 6/1993 | Kamerling | 606/48 |
| 5,254,121 | A | 10/1993 | Manevitz et al. | 606/128 |
| 5,277,201 | A | 1/1994 | Stern | 607/98 |
| 5,277,696 | A | 1/1994 | Hagen | 606/49 |
| 5,281,216 | A | 1/1994 | Klicek | 606/42 |
| 5,281,218 | A | 1/1994 | Imran | 606/41 |
| 5,330,470 | A | 7/1994 | Hagen | 606/42 |
| 5,348,554 | A | 9/1994 | Imran et al. | 606/41 |
| 5,366,443 | A | 11/1994 | Eggers et al. | 604/114 |
| 5,403,311 | A | 4/1995 | Abele et al. | 606/49 |
| 5,419,767 | A | 5/1995 | Eggers et al. | 604/114 |
| 5,454,809 | A | 10/1995 | Janssen | 606/41 |
| 5,458,596 | A | 10/1995 | Lax et al. | 606/31 |
| 5,514,130 | A | 5/1996 | Baker | |
| 5,520,685 | A | 5/1996 | Wojciechowicz | 606/49 |
| 5,522,815 | A | 6/1996 | Durgin, Jr. et al. | 606/50 |
| 5,556,397 | A | 9/1996 | Long et al. | 606/48 |
| 5,643,255 | A | 7/1997 | Organ | |
| 5,658,279 | A | 8/1997 | Nardella et al. | 606/45 |
| 5,683,366 | A | 11/1997 | Eggers et al. | 604/114 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 604/114 |
| 5,697,909 | A | 12/1997 | Eggers et al. | 604/114 |
| 5,785,705 | A | 7/1998 | Baker | |
| 5,814,044 | A * | 9/1998 | Hooven | 606/48 |
| 5,925,045 | A * | 7/1999 | Reimels et al. | 606/48 |
| 5,944,715 | A * | 8/1999 | Goble et al. | 606/41 |
| 6,135,999 | A | 10/2000 | Fanton et al. | |
| 6,149,620 | A * | 11/2000 | Baker et al. | 604/22 |
| 6,254,600 | B1 * | 7/2001 | Willink et al. | 606/412 |

* cited by examiner

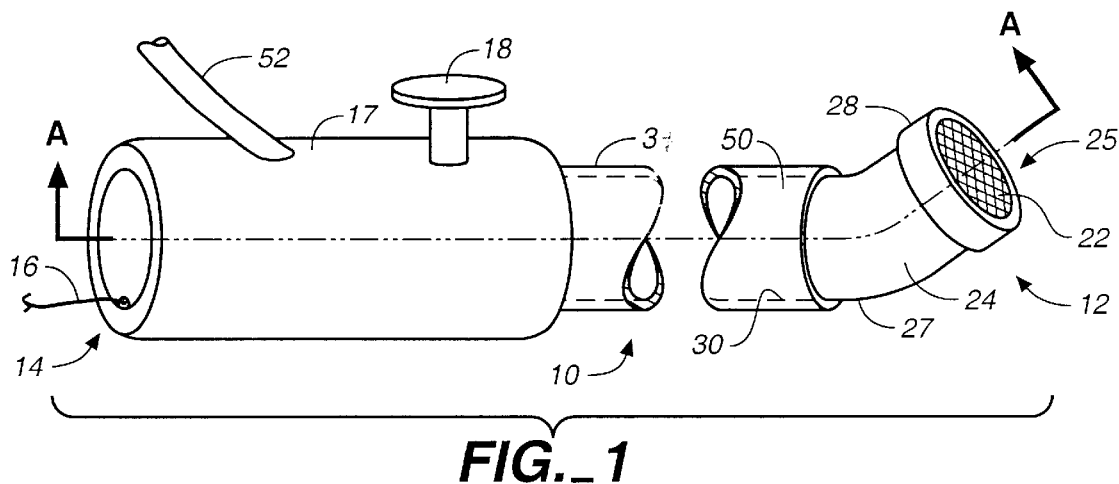
FIG._1
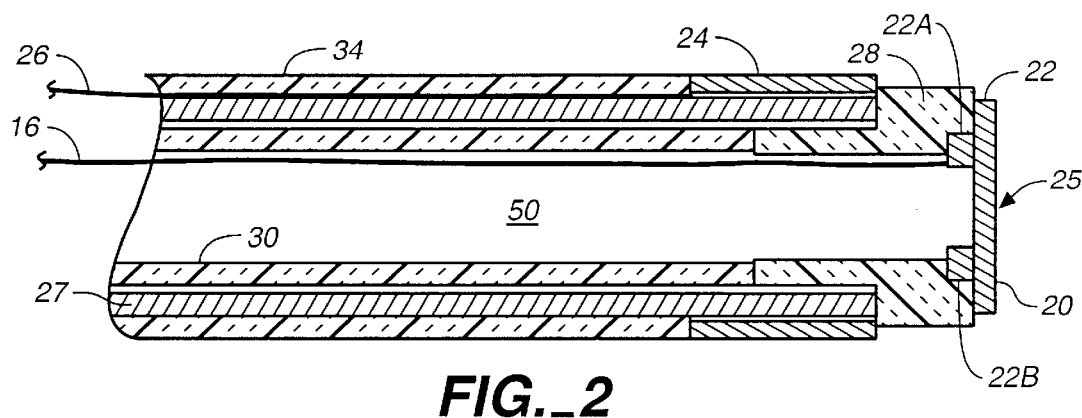
FIG._2
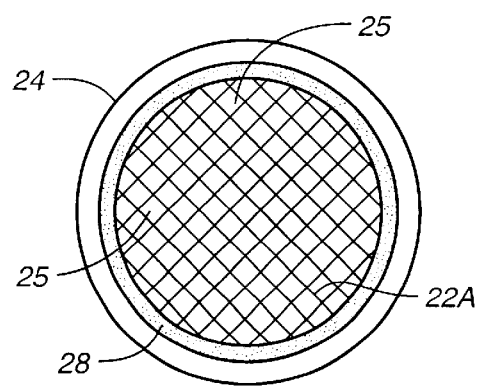
FIG._3
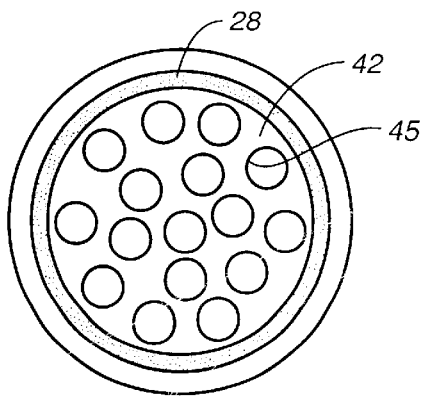
FIG._4

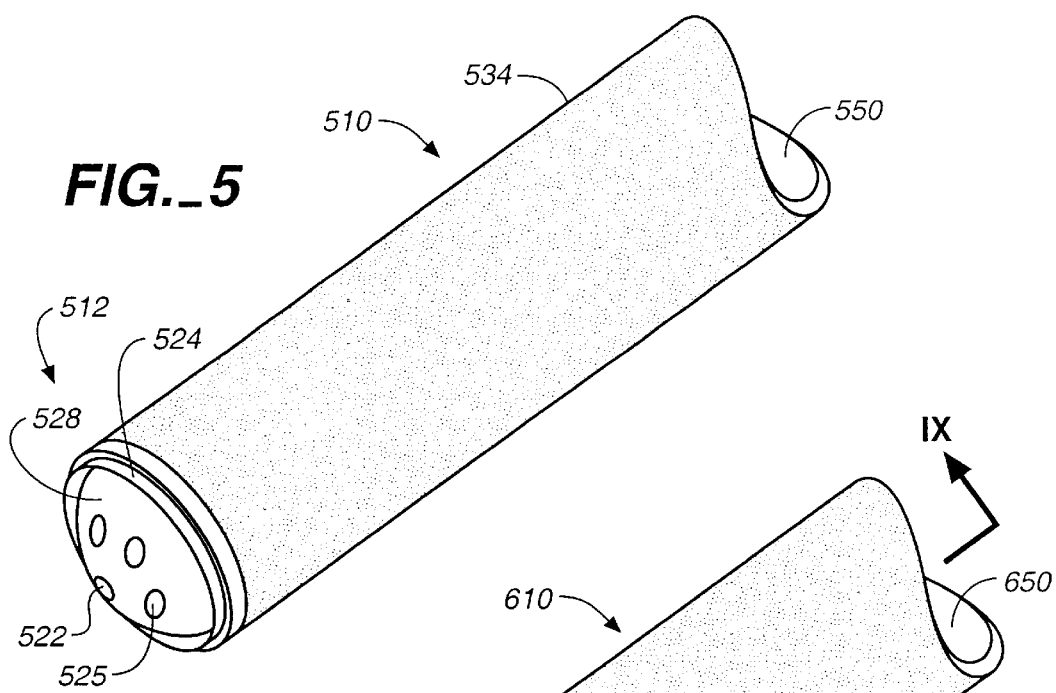
FIG._5
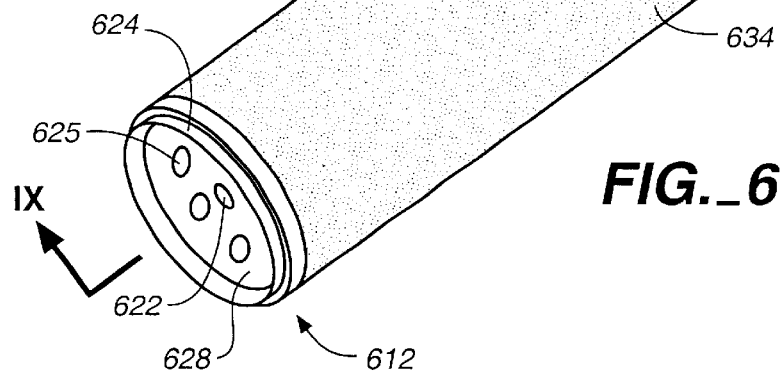
FIG._6
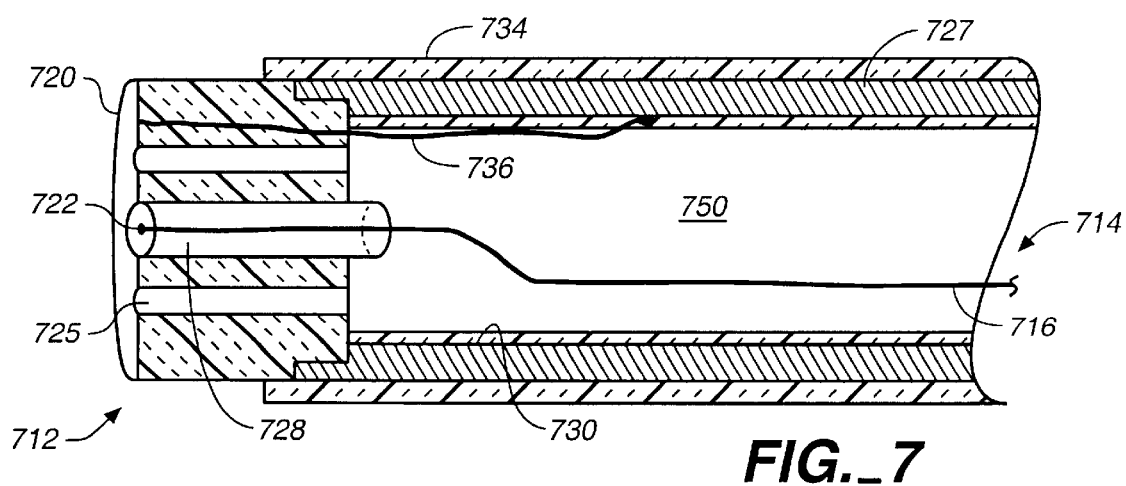
FIG._7

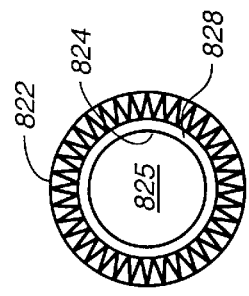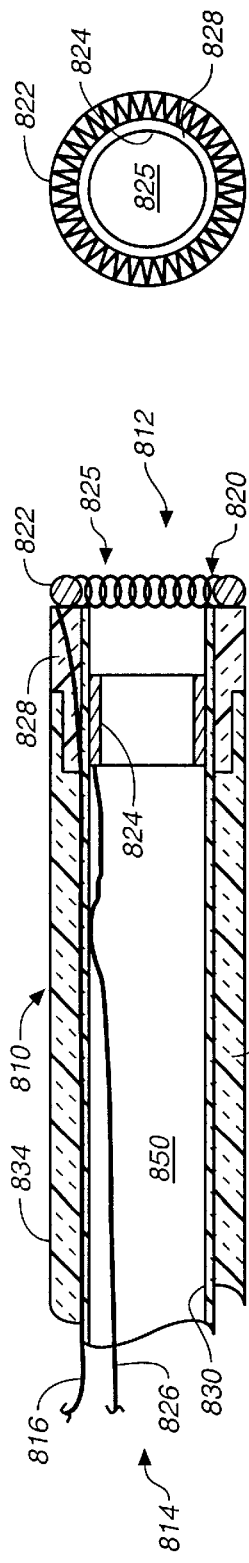
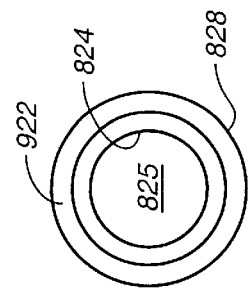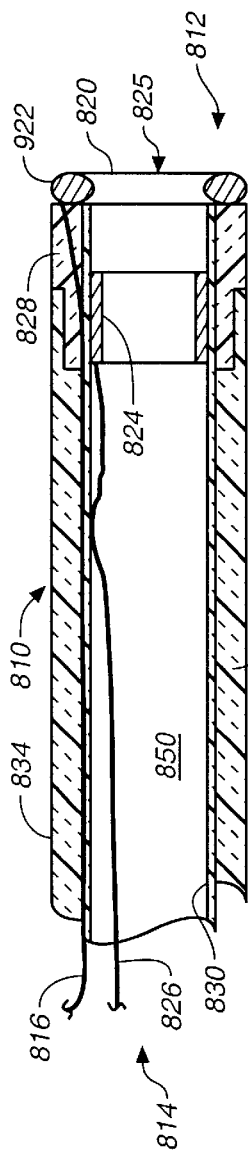
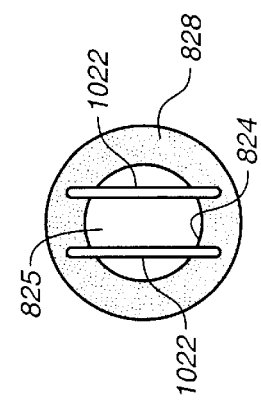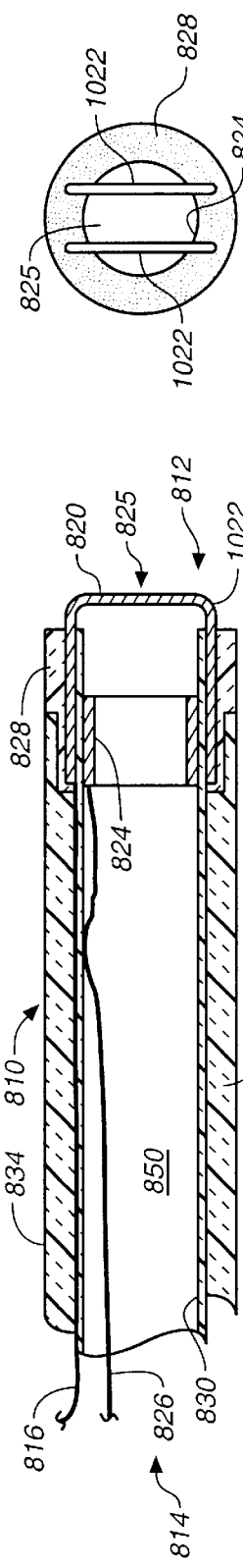

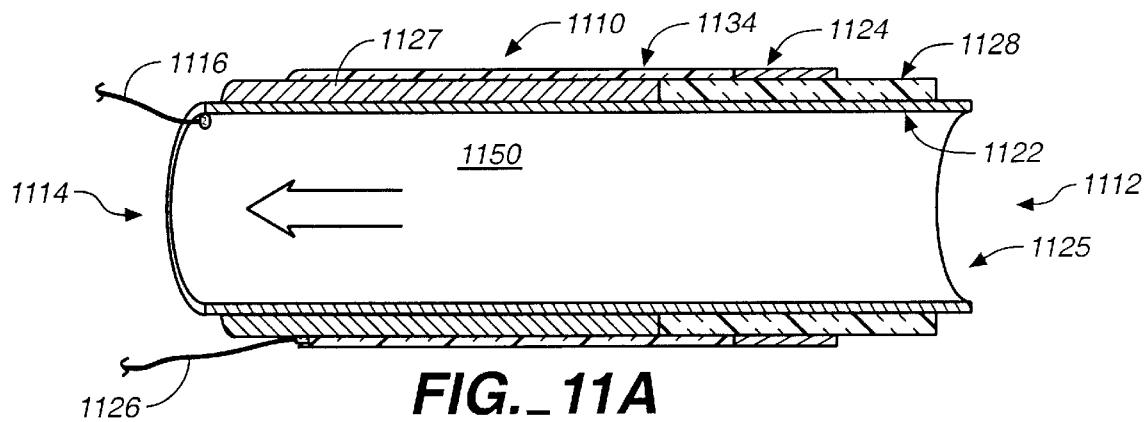
FIG._11A
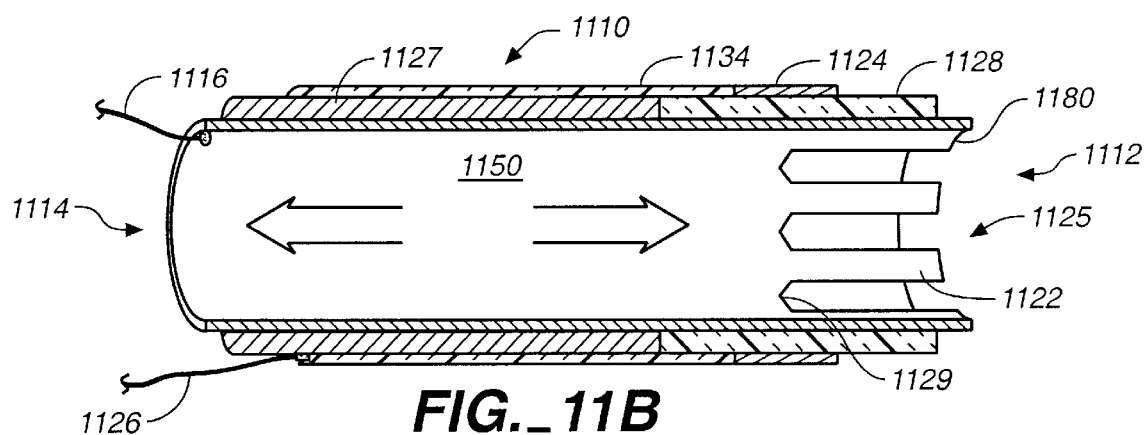
FIG._11B
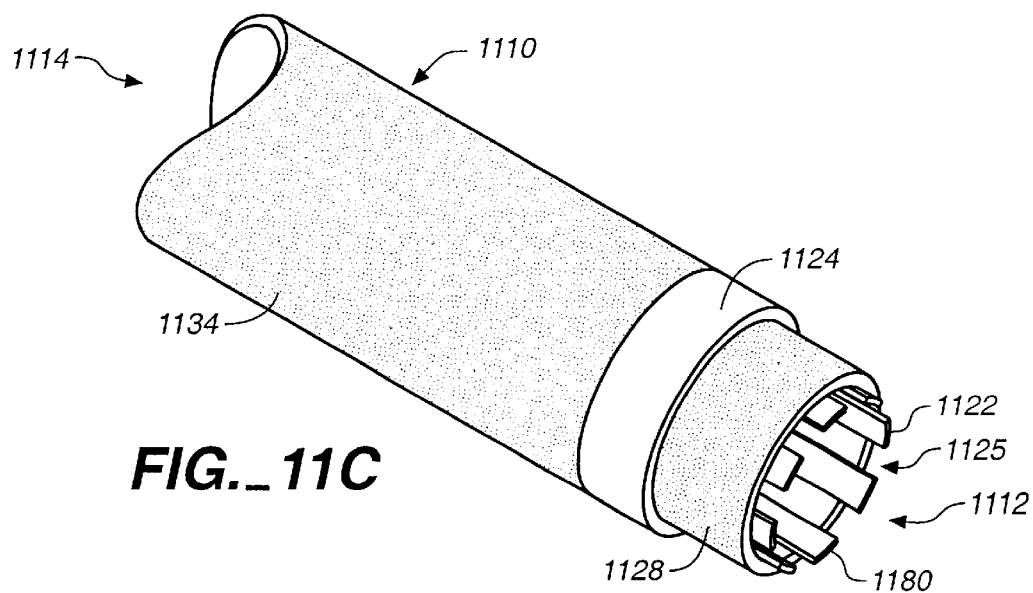
FIG._11C

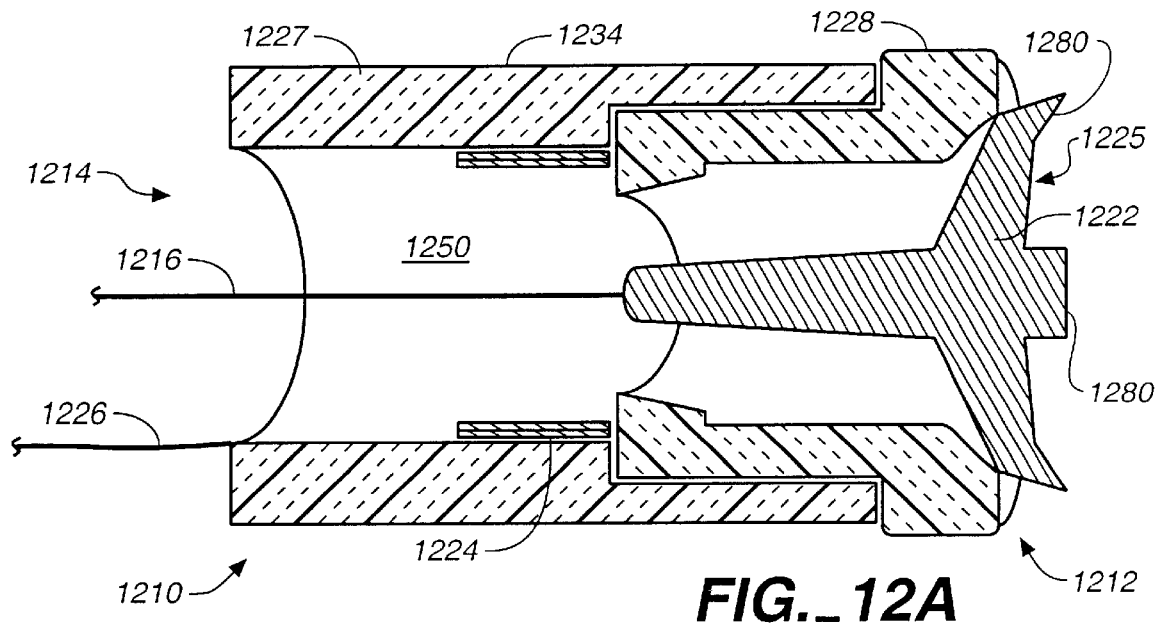
FIG._12A
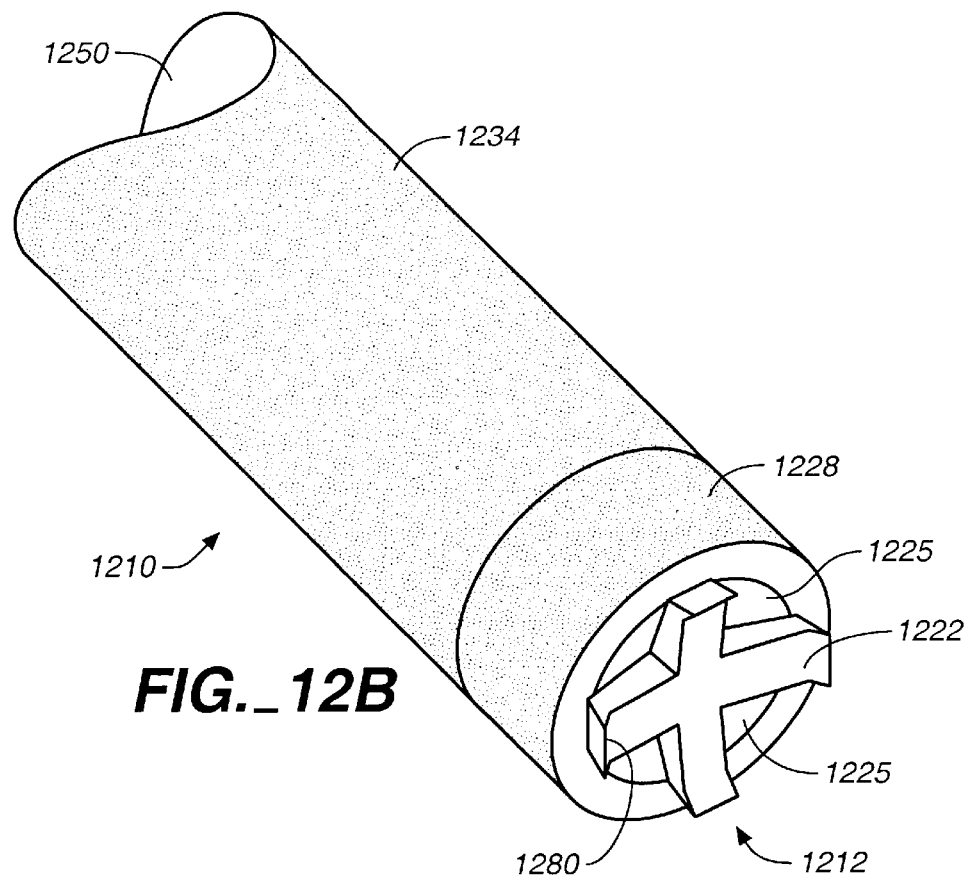
FIG._12B

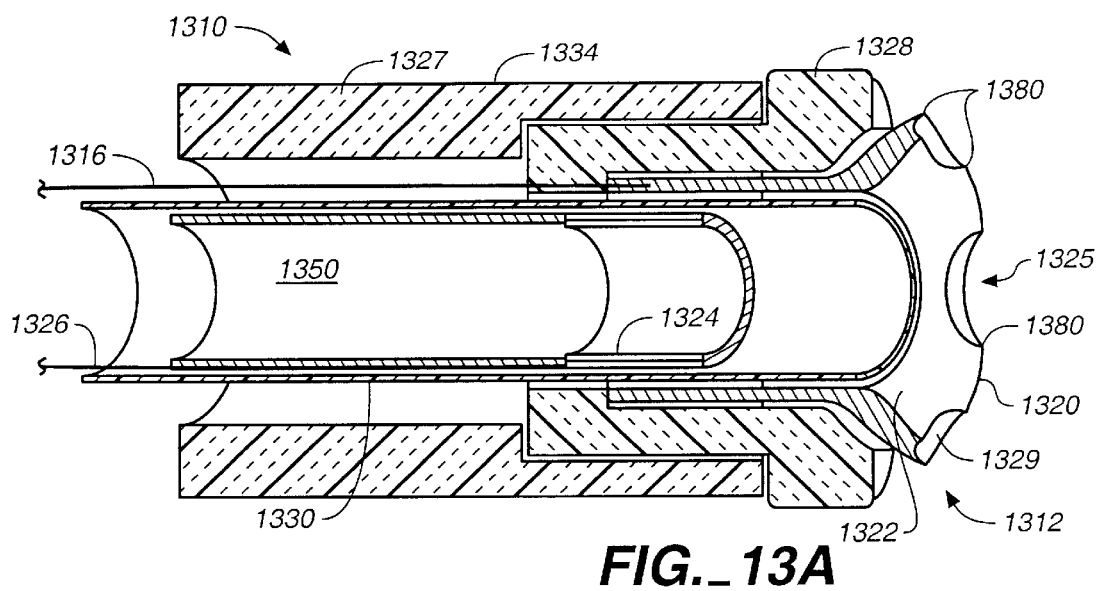
FIG._13A
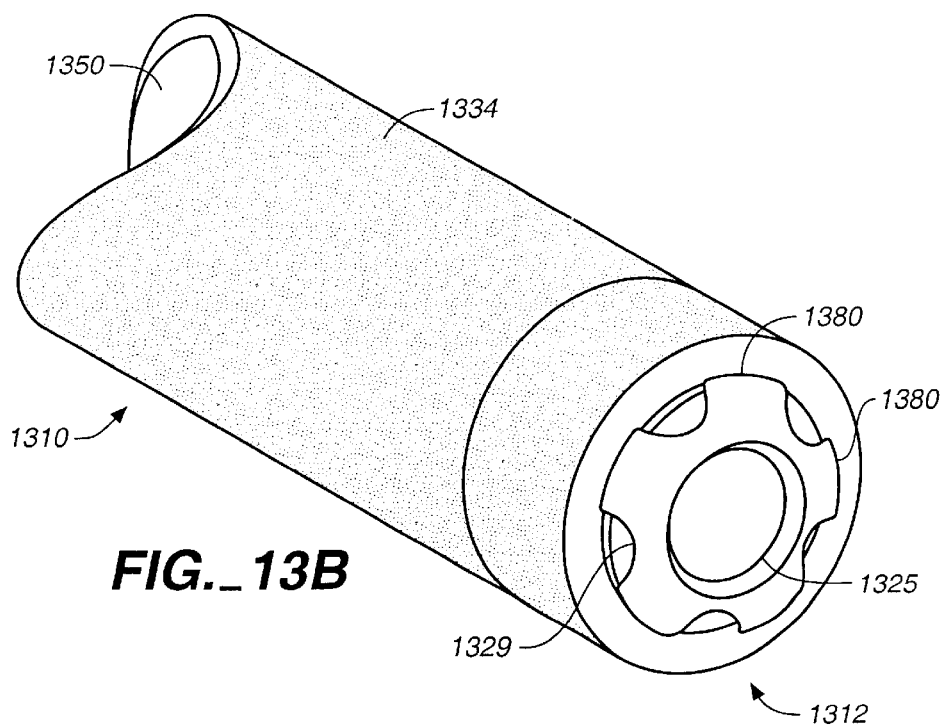
FIG._13B

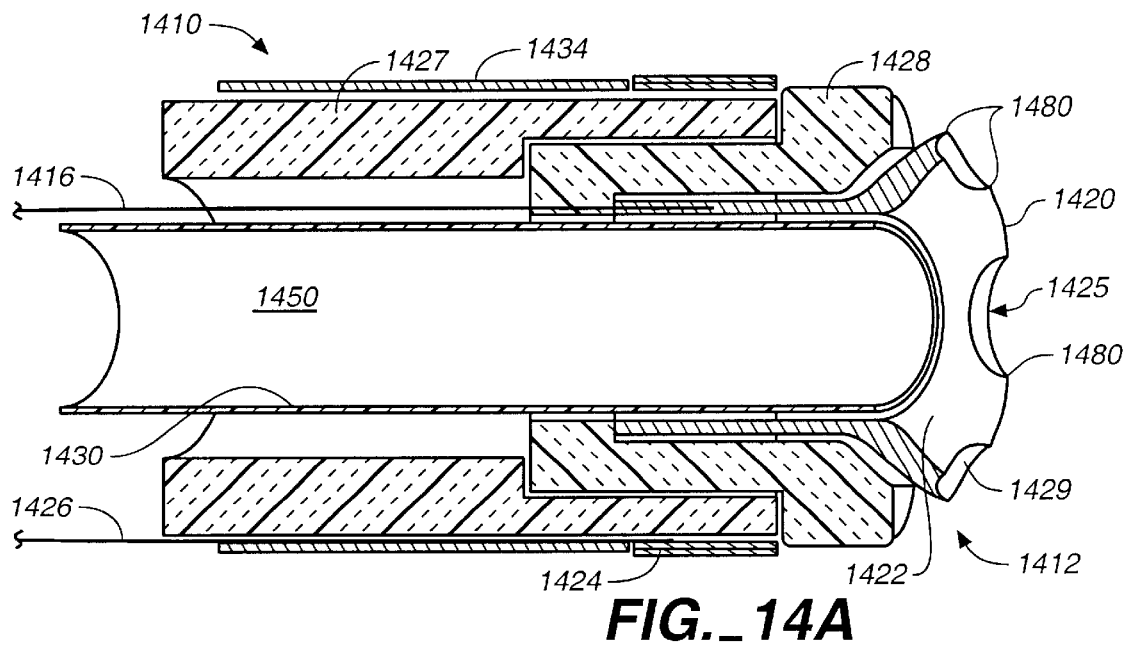
FIG._14A
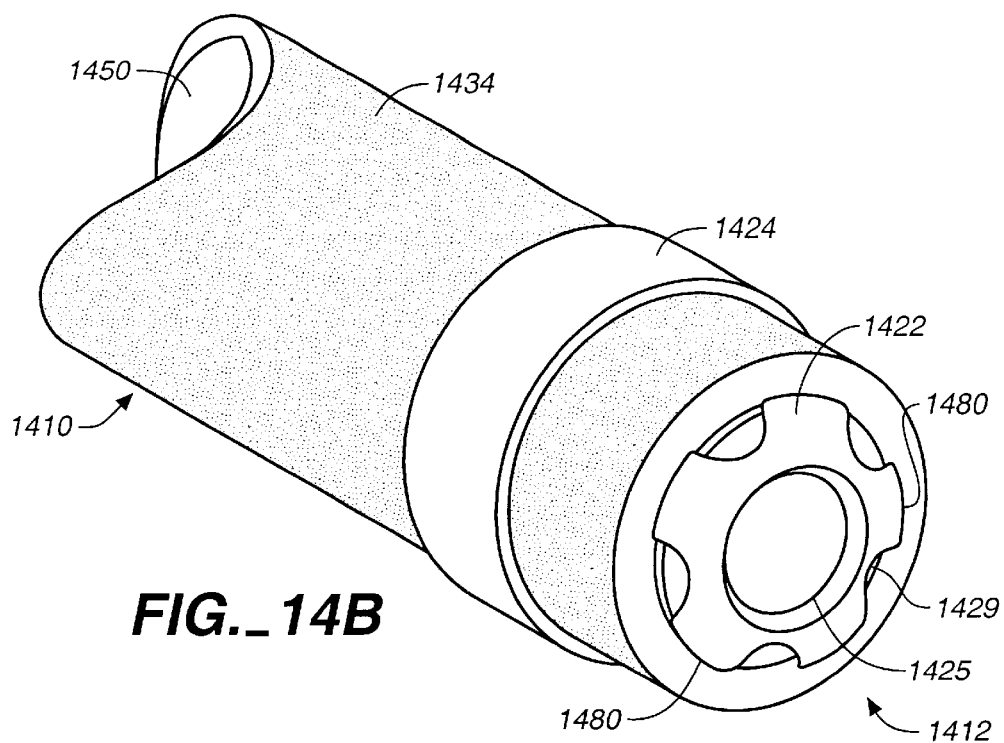
FIG._14B

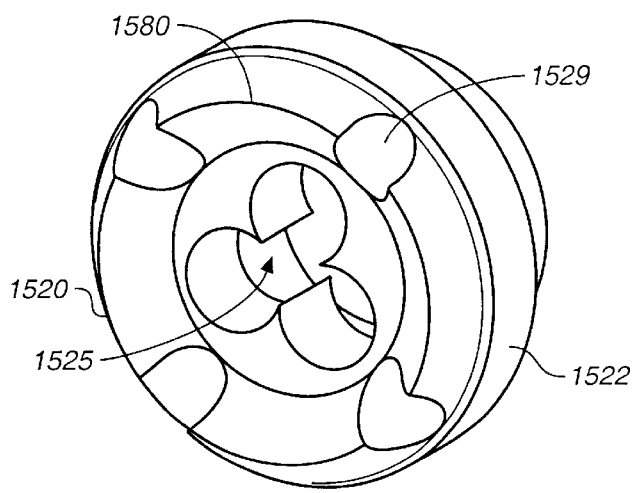
FIG._15A
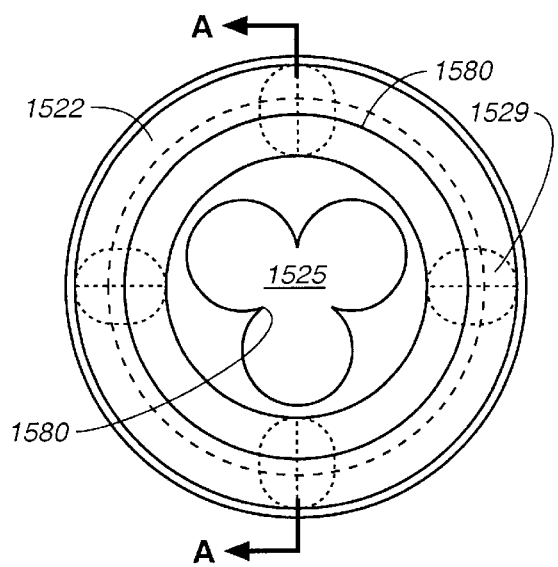
FIG._15B
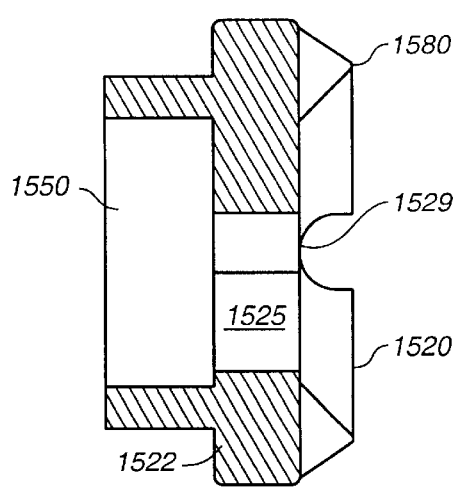
FIG._15C

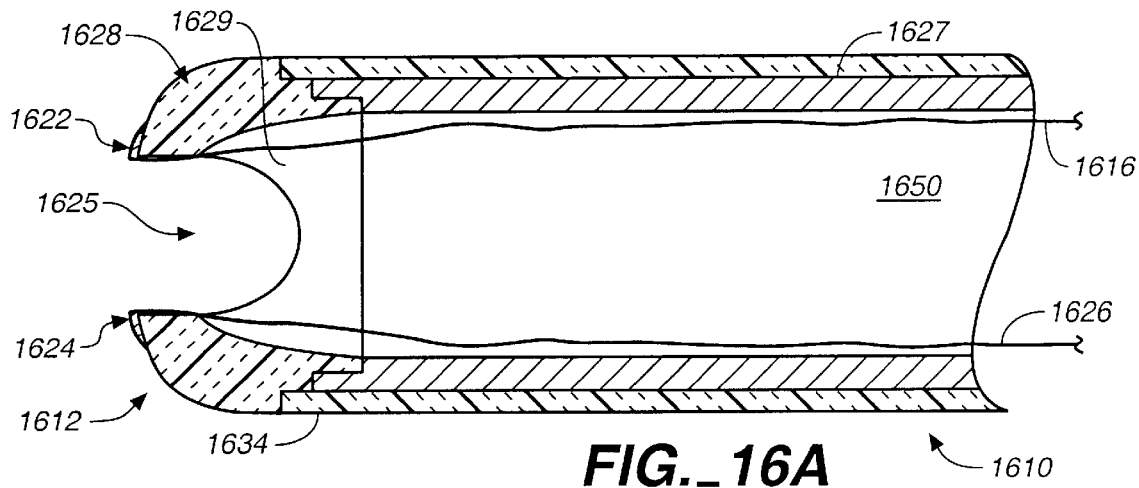
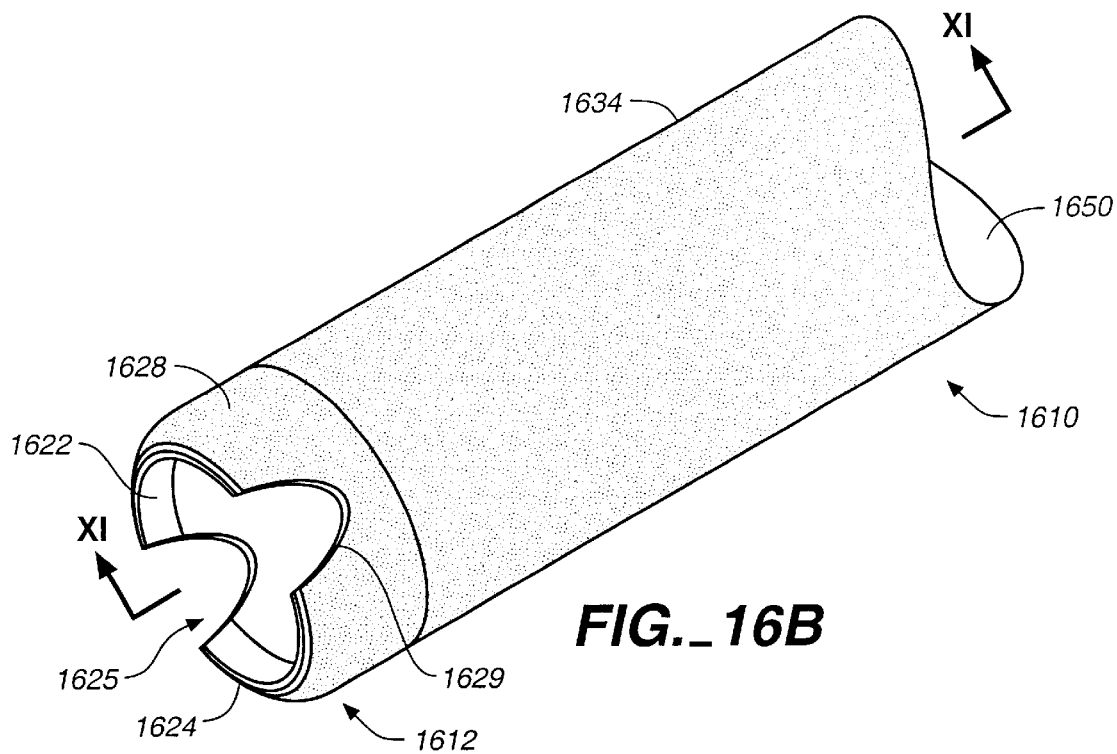

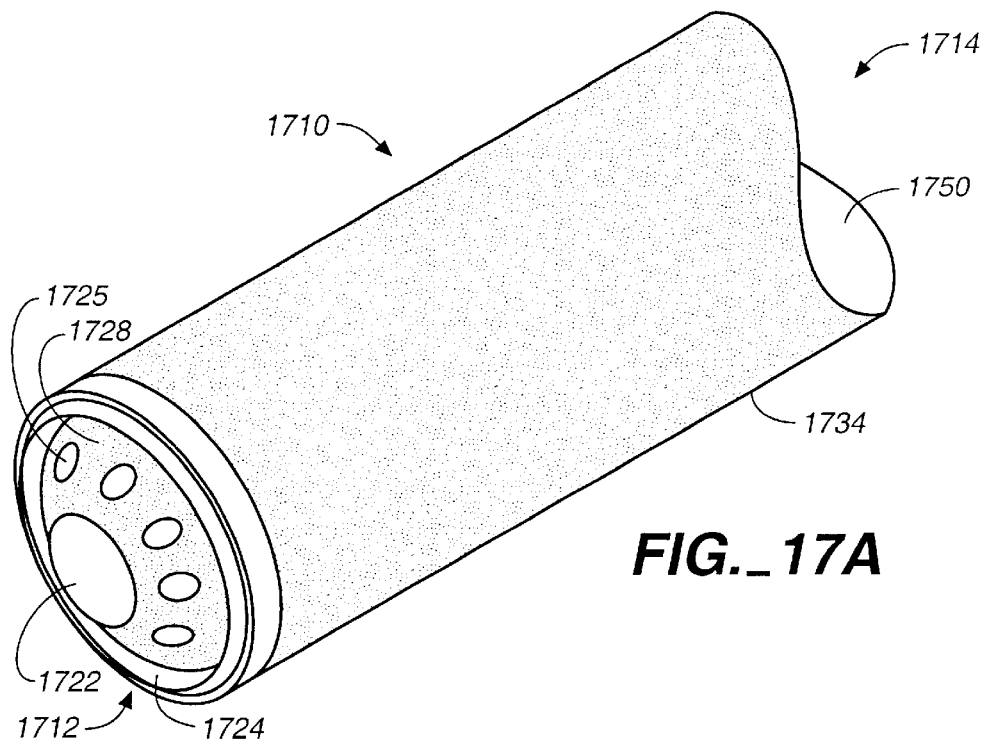
FIG._17A
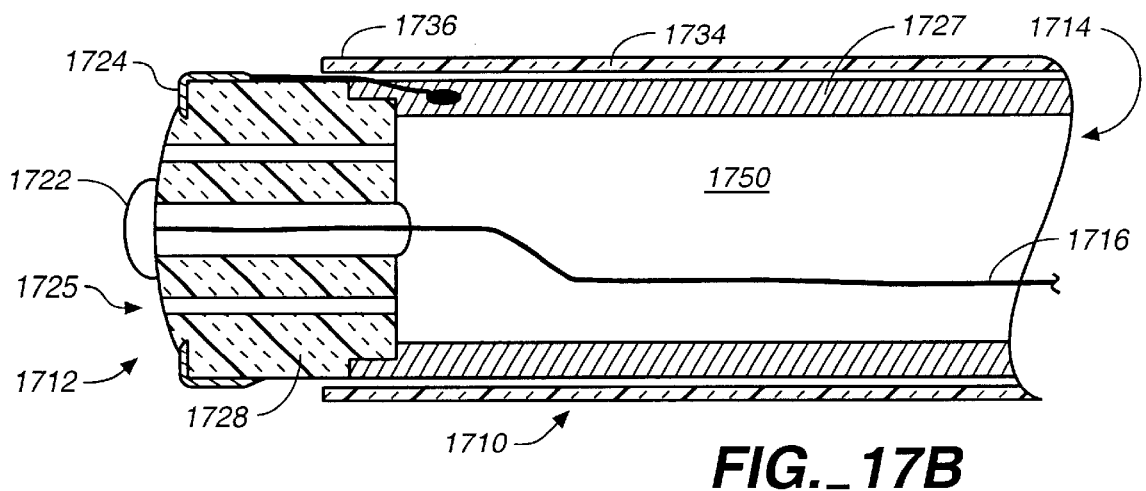
FIG._17B

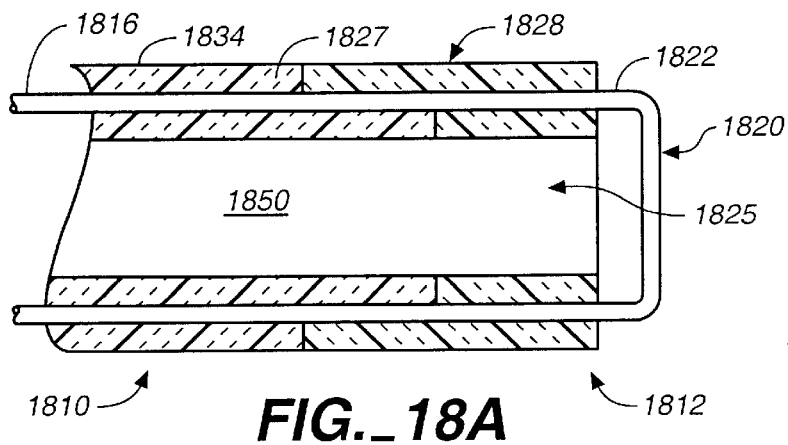
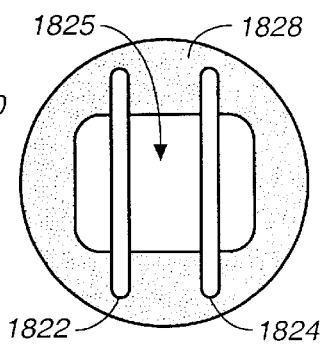
FIG._18A  FIG._18B
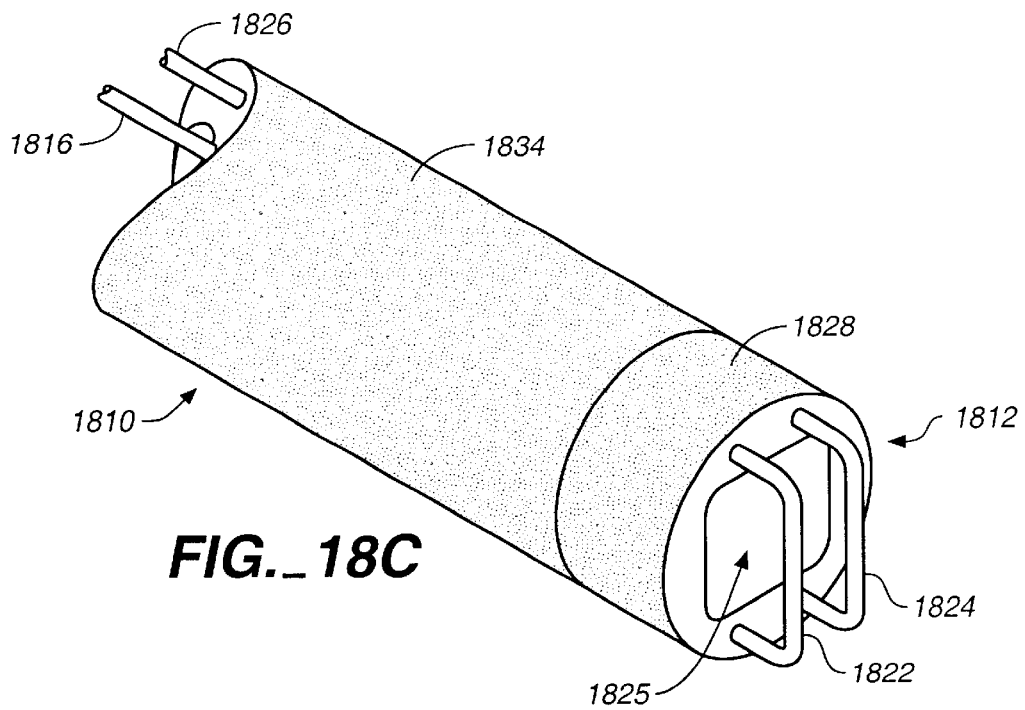
FIG._18C

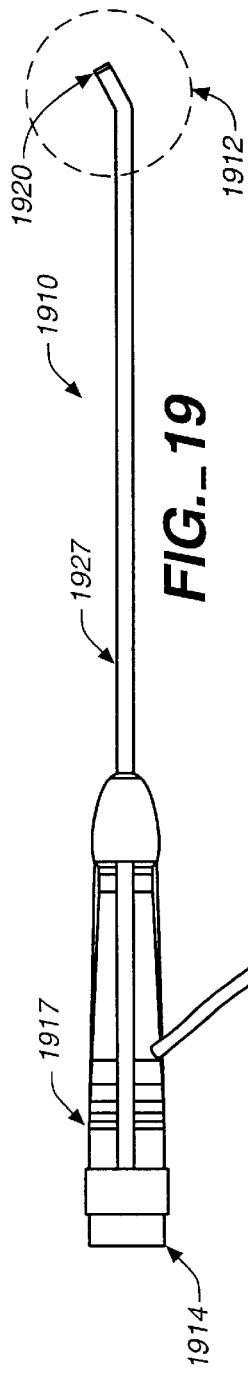
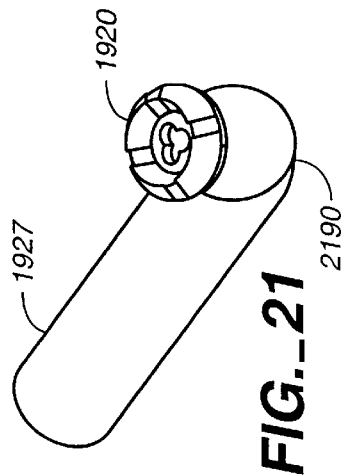
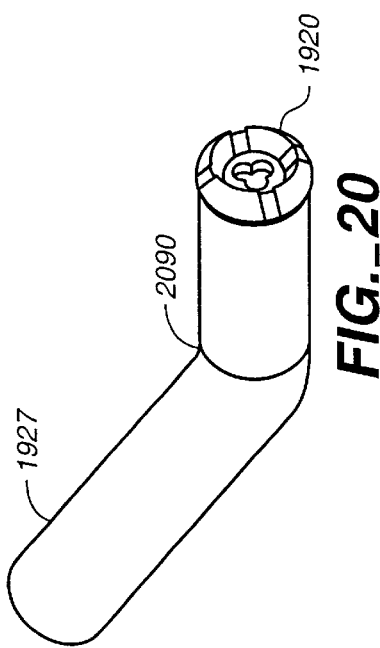
FIG._19
FIG._21
FIG._20

SURGICAL INSTRUMENT FOR ABLATION AND ASPIRATION

BACKGROUND

The present invention relates to electrosurgical instruments and systems for treating a surgical site on a human or animal body such as biological tissue by the application of energy. More particularly, the invention relates to surgical devices and methods for applying high frequency energy to modify the characteristics of the tissue such as by ablation in combination with aspiration of any by-products from a surgical site.

Numerous surgical instruments for the treatment of biological tissue through the application of energy in a wide variety of medical procedures are known in the art. For example, U.S. Pat. No. 4,593,691 to Lindstrom et al., U.S. Pat. No. 4,033,351 to Hetzel, and U.S. Pat. No. 5,403,311 to Abele et al. are examples of electrosurgical probes for use during an electrosurgical procedure such as for cutting or ablating tissue. U.S. Pat. No. 5,458,596 to Lax et al. shows an example of an electrosurgical probe for the contraction of tissue by delivering electrical energy to the treatment tissue. Also, U.S. Pat. No. 3,828,780 to Morrison and U.S. Pat. No. 5,277,696 to Hagen show electrosurgical instruments which deliver electrical energy for coagulation during surgical procedures.

The use of these instruments typically involves the transmission of energy to a distal end of the electrosurgical probe or instrument. The distal end is inserted into the body to a surgical site of a patient to apply energy during the procedure. The frequency, power, and voltage generated by the electrical instrument and transmitted to the distal end are selected depending on the type of procedure for which the instrument is being used. For instance, such instruments are used for a variety of procedures such as heating, softening, shrinking, cutting and ablating tissue.

Because such instruments may be used for different procedures, the tissue (or other body part) being treated may respond differently depending on the treatment being performed. For instance, if the instrument is used to ablate the tissue, smoke and charring may be generated during the procedure or residual tissue debris may remain after treatment. Unwanted air bubbles or excess fluid may also be present in the treatment area that may interfere with effective treatment of the tissue and should be removed from the surgical site during the procedure. Thus, it is desirable to provide an electrosurgical device for aspirating the region being treated to remove smoke, tissue debris, excess fluid and other unwanted matter from the tissue site being treated.

During the usage of prior instruments, however, such as in numerous of the above-mentioned instruments, the removal of unwanted matter generally requires the separate provision of an aspiration device. The use of two separate instruments increases the treatment time because the suction instrument must be separately inserted into the surgical site, used, and removed from the site before and/or after the electrosurgical treatment instrument is inserted or used at the site. Additionally, a separate suction instrument may be inserted into the surgical site through another access point which creates another portal in the patient's body which possibly creates further complications such as infection and scarring.

U.S. Pat. No. 5,520,685 to Wojciechowicz, U.S. Pat. No. 4,682,596 to Bales and U.S. Pat. No. 4,347,842 to Beale disclose suction devices in various combinations and configurations with the electrosurgical probe. U.S. Pat. No. 5,195,959 to Smith also discloses an electrosurgical device with suction and irrigation to supply electrically conductive fluid which adds even more material to the surgical site and would need to be removed during the procedure. Wojciechowicz, in particular discloses a suction coagulator with a suction lumen for the suction of by-products of electrosurgery through the instrument through a tip. Further, Hagen discloses a suction device for aspirating fluid through the surgical probe.

However, the arrangement of the suction lumen in relationship to the electrosurgical portion is such that blockage or clogging of the suction lumen can occur which could complicate the surgical procedure and unwanted or unnecessary ablation could occur. Charred and ablated tissue and coagulated blood often clog the tips of electrosurgical devices.

Therefore, it would be desirable to provide an instrument that may be used not only to treat a patient but also to aspirate the treatment area during treatment to simultaneously remove unwanted material. The surgical device and method should be simple and operate in a standard surgical environment. The electrosurgical instrument should provide the surgeon the ability to ablate, cut or coagulate in the same device while providing a suction means to aspirate surgical by-products from the surgical site. The suction and aspiration should be anti-clogging such that the device does not cause unwanted nor undesirable effects due to blockage. Such instrument and method should be able to precisely treat biological tissue with energy while efficiently allowing the surgeon to perform the medical procedure quickly without the need to utilize multiple instruments for the treatment.

SUMMARY

It is, therefore, an object of the present invention to provide a surgical instrument and method for the application of energy to a treatment area of a patient and for the aspiration of unwanted matter, such as smoke, air bubbles and biological waste debris from the surgical site.

It is a related object of the present invention to provide a combination of electrosurgical and aspiration instrument that provides an energy application surface area that applies energy uniformly over the treatment area and also permits aspiration therethrough so as to limit clogging.

It is another object of the present invention to provide a combination electrosurgical and aspiration instrument having both an active electrode and a return electrode at a distal tip of the instrument such that energy distribution is substantially limited to the distal tip surface.

These and other objects and features are accomplished in accordance with the principles of the present invention by providing a probe having a cannula with at least one electrode for the transmission and application of energy to a treatment site along an energy application surface as well as a suction lumen through which unwanted matter and surgical by-products may be aspirated from the treatment area. Preferably, at least one electrode, an active electrode is provided on a distal end of the probe. A return or indifferent electrode may located on the patients' body or on the probe. The instrument is coupled to an energy generator that preferable includes controls that may be used to regulate the power, frequency, and voltage applied to the instrument to vary the type of treatment for which the instrument is used. The regulation may include feedback controls.

In one embodiment of the invention, the active electrode is provided with a plurality of small passages therethrough in a fluid communication with the suction lumen of the instrument. An active electrode with such aspiration passages may be in the form of a mesh, a disc having perforations therethrough, or plural conductors supported by an insulator with apertures therethrough. Thus, aspiration of the treatment area occurs through at least a portion of the energy application surface. If desired, both the active and return electrodes may be positioned in substantially the same plane such that energy distribution is substantially restricted to a substantially planar surface area, such as the surface area of the distal tip.

In an alternative embodiment of the present invention, the surgical instrument has a shaft having distal and proximal ends. The shaft also defines at least one lumen. The lumen has at least one aspiration opening at the distal end. An active electrode is located at the distal end of the shaft which defines an energy application surface. The active electrode is electrically coupled to a power source. A return electrode is coupled to the power supply such that a current path from the active electrode to the return electrode passes over the aspiration opening to prevent clogging of the opening. The return electrode may be located on a portion of the body of a patient or on the shaft.

As negative pressure is applied to the lumen, matter that is in the surgical site is aspirated through the aspiration opening. The opening is configured to prevent clogging of the aspirated matter at the distal end. The aspiration opening may be defined by the active electrode which is configured to prevent clogging of the aspiration opening and allow continued desiccation of the unwanted aspirated matter such that the matter will move easily through the aspiration lumen.

These and other features and advantages of the present invention will be readily apparent from the following drawings and detailed description of the invention, the scope of the invention being set out in the appended claims.

BRIEF DESCRIPTION OF THE DRAWINGS

The detailed description will be better understood in conjunction with the accompanying drawing, wherein like reference characters represent like elements, as follows:

FIG. 1 is a perspective view of an electrosurgical aspiration instrument formed in accordance with the principles of the present invention;

FIG. 2 is a cross-sectional view along axis A—A of FIG. 1;

FIG. 3 is an end view of a distal tip of the instrument of FIG. 1;

FIG. 4 is an end view of a distal tip of the instrument of FIG. 1 showing an alternative tip embodiment;

FIG. 5 is a perspective view of an electrosurgical aspiration instrument according to the present invention with a distal tip active electrode having a convex configuration;

FIG. 6 is a perspective view of an electrosurgical aspiration instrument according to the present invention with a distal tip active electrode having a concave configuration;

FIG. 7 is a cross-sectional view of a basic distal tip portion of the instrument of FIGS. 5 and 6.

FIGS. 8A and 8B are cross-sectional and end views, respectively, of an electrosurgical aspiration instrument showing one embodiment of an active electrode in a coil configuration with an internal return electrode;

FIGS. 9A and 9B are cross-sectional and end views, respectively, of an electrosurgical aspiration instrument according to the present invention showing an active electrode in a ring configuration with an internal return electrode;

FIGS. 10A and 10B are cross-sectional and end views, respectively, of an electrosurgical aspiration instrument according to the present invention showing one embodiment of an active electrode in a prong configuration with an internal return electrode;

FIGS. 11A–C are cross-sectional and perspective views, respectively, of an electrosurgical aspiration instrument according to present invention having a mechanical grating configuration of the active electrode with an external return electrode; FIG. 11A is a ring grating configuration; FIG. 11B is a rasp grating configuration;

FIGS. 12A and 12B are cross-sectional and perspective views, respectively, of an electrosurgical aspiration instrument with an alternative embodiment showing an active electrode having a cross configuration for mechanical grating and delivery of energy;

FIGS. 13A and 13B are cross-sectional and perspective views, respectively, of an alternate aspiration instrument of FIGS. 12A and 12B with an active electrode having an ashtray configuration for mechanical grating and energy delivery with an internal return electrode;

FIGS. 14A and 14B are cross-sectional and perspective views, respectively, of the instrument of FIGS. 13A and 13B showing an external return electrode;

FIGS. 15A–C are detailed perspective, end, and cross-sectional views of the distal tip of an electrosurgical aspiration instrument according one embodiment of the present invention; FIG. 15A is a detailed perspective view of an active electrode with an aspiration opening; FIG. 15B is an end view of the active electrode; and FIG. 15C is a cross-sectional view along line A—A of the active electrode of FIG. 15B;

FIGS. 16A and 16B are cross-sectional and perspective views of an alternative embodiment of the instrument present invention wherein the distal tip is a true bipolar configuration having a single aspiration opening;

FIGS. 17A and 17B are perspective and cross-sectional views of an alternate embodiment of the instrument according to the present invention showing a true bipolar configuration of the distal tip having multiple aspiration openings;

FIGS. 18A–C are cross-sectional, end and perspective views of an alternative embodiment of the distal tip having a single aspiration opening with both active and return electrodes formed by loop prongs defining the energy application surface;

FIG. 19 is a perspective view of the complete electrosurgical instrument of the present invention showing a probe having a handle and a shaft with a distal tip for treatment with a suction line and control; and FIGS. 20 and 21 are alternative embodiments of the distal end shaft of FIG. 19 according to the present invention having a pre-bent distal end in a 30 degree configuration and a 90 degree configuration, respectively.

DETAILED DESCRIPTION OF THE INVENTION

An embodiment of an electrosurgical aspiration instrument 10 capable of aspirating a patient treatment area within a standard surgical environment in accordance with the principles of the present invention is illustrated in FIGS. 1 and 2. Electrosurgical aspiration instrument 10 is in the form of a probe having, generally, a shaft 27 disposed along longitudinal axis A—A, a distal end 12 at which treatments are performed and a proximal end 14 at which instrument 10 is coupled to a power source (not shown) via power line 16.

Power line 16 supplies energy to distal end 12 for treatment. The power source preferably permits modification and adjustment of the power, frequency, and voltage of the energy transmitted to distal end 12. A handle 17 may be provided to facilitate grasping of instrument 10 adjacent proximal end 14. At least one actuator 18, such as an aspiration control valve or switch or a power button may be provided. In a preferred embodiment, a foot pedal (not shown) is provided to control power supplied to distal end 12 and actuator 18 controls aspiration through the instrument. Additional actuators or controllers, such as for adjusting the power, frequency, or voltage, may be provided either on instrument 10 itself or on the power source if desired.

Electrosurgical aspiration instrument 10 has an energy application surface or plane 20 formed by at least one electrode that applies energy to the patient area to be treated. In one embodiment, instrument 10 has at least two electrodes, active electrode 22 and return electrode 24 that cooperate to apply energy across surface 20. Electrodes 22 and 24 are formed from electrically conductive materials, for example a medical grade stainless steel, capable of withstanding the high temperatures resulting from use of instrument 10. It will be appreciated that the material that is selected for electrodes 22 and 24 has defined conductivity characteristics that affects the power necessary to achieve the desired treatment operation.

As shown in FIGS. 1 and 2, active electrode 22 is positioned at the open distal end of shaft 27 of electrosurgical aspiration instrument 10. Although shaft 27 may be a separate element, preferably, return electrode 24 serves a dual purpose as both the return electrode that completes the energy circuit with active electrode 22 as well as the shaft of instrument 10. It will be appreciated that the arrangement of electrodes 22 and 24 may be reversed, such that the active electrode is in the form of a shaft with an open distal end on which the return electrode is positioned. Alternatively, the return electrode may be located on a point external to the treatment site such as placing a grounding pad or plate on the body (not shown).

Power is transmitted to active electrode 22 from power line 16 via a conductive element 26, such as a wire, as shown in FIG. 2. Return electrode 24, as described above, is preferably in the form of an electrically conductive shaft, preferably formed from 304 stainless steel or any other biocompatible conductive material, that extends from distal end 12 of instrument 10 to proximal end 14. The end of return electrode 24 adjacent proximal end 14 of instrument 10 is coupled to the power source to communicate the power source at proximal end 14 with distal treatment end 12 and thereby to complete the energy supply circuit of electrosurgical aspiration instrument 10. If desired, the shaft forming a return electrode 24 may be formed from a malleable material so that it is shapeable by the user. However, the distal-most end of instrument 10 should not be flexible. Additionally, any bend imparted to instrument 10 should not be so extreme as to close off the lumen formed therethrough and described in further detail below.

Electrodes 22 and 24 are electrically isolated from each other such that electrical arcing between active electrode 22 and return electrode 24 generates treatment energy along energy application surface 20 that may be applied to the patient. Electrical isolation or insulation of electrodes 22 and 24 at energy application surface 20 may be accomplished by the provision of insulator 28 therebetween. Insulator 28 is formed from many desired insulative material, such as ceramic, teflon or pyrolytic carbon, that may withstand the high temperatures that may result upon application of energy at distal end 12 during use of the instrument 10. Preferably, active electrode 22, return electrode 24, and insulator 28 permit fluid communication through instrument 10 from the treatment area at which energy application surface 20 is applied to proximal end 14, as described in further detail below.

In addition, electrodes 22 and 24 must also be electrically isolated axially along longitudinal axis 11 between proximal end 14 (at which instrument 10 applies treatment energy) so that power supply to energy application surface 20 is not shorted. Although insulation on wire 26 is typically sufficient to electrically insulate active electrode 22 from return electrode 24, optional insulation 30 on interior surface 32 of return electrode 24 may be provided. Insulation 30 is selected from biocompatible and electrically insulative material which could include nylon, polyimide or other shrink tubing and also functions to limit the heat transfer to the shaft. If active electrode 22 (rather than return electrode 24) is coupled to the power source via a conductive shaft as mentioned above and described with respect to the embodiments of FIGS. 8–11, insulation 30 would be more desirable. An insulative cover 34, such as formed from a teflon coating or a heat shrink cover, is provided over exterior surface 36 of return electrode 24 to restrict the extent of arcing and hence energy supplied to distal treatment end 12 of instrument 10.

Instrument 10 may be substantially straight, or may have a slight bend at distal end 12 such that energy application surface 20 is slightly offset form longitudinal axis 11. As shown in FIGS. 1 and 2, the energy application surface 20 of electrosurgical aspiration instrument 10 extends along distal end 12 (approximately transverse to longitudinal axis A—A in a straight instrument). However, it will be appreciated that electrodes 22 and 24 may be provided at different positions at distal end 12 to alter the location of energy application surface 20.

Electrosurgical aspiration instrument 10 may be used for a variety of electrosurgical treatments. On particular use of instrument 10 is for ablation of human or animal tissue. Because ablation generally occurs at very high temperatures, e.g. 300–1000 degrees Celsius, smoke and/or vapor may be generated during ablation. It may be desirable to remove smoke; unwanted or excess gases, such as air bubbles; fluids, such as irrigation fluid required to irrigate or enhance conduction after treatment; from the treatment area during treatment. Moreover, debris or other materials or biological elements may remain after the ablation procedure that should be removed from the treatment area. Thus, in accordance with the principles of the present invention, instrument 10 is also designed to aspirate such unwanted matter from the treatment area during the electrosurgical procedure performed thereby. It will be appreciated that aspiration may be performed either simultaneously with, before, or after electrosurgical treatment of an area. Further, it should be appreciated that a power source may be used which sequentially, or in a predetermined sequence, supplies power to the active electrode and then provides power for aspiration. Accordingly, an aspiration lumen 50 is provided within electrosurgical aspiration instrument along longitudinal axis A—A. Aspiration lumen 50 may be formed by interior wall or surface 32 of return electrode 24 and is in fluid communication with a aspiration line 52 which couples proximal end 14 of instrument 10 with a vacuum source of other aspiration device (not shown). Aspiration line 52 is preferably standard tubing for connection to a suction source and device.

In order to facilitate aspiration during electrosurgical treatment, such as during ablation or coagulation, instrument 10 is provided with an aspiration means which permits aspiration through energy application surface 20. This is accomplished by providing at least one through-hole or aperture 25 through active electrode 22 which defines surface 20. Alternatively, a plurality of through-holes or apertures through active electrode 22 may be used to aid in aspiration of the electrosurgical probe. In the embodiment of FIGS. 1 and 2, active electrode 22 is in the form of a wire mesh or screen 22A supported by an electrically conductive ring 22B. Mesh 22A and ring 22B comprising active electrode 22 are formed from a conductive materials, such as stainless steel, tungsten, or titanium or their alloys, that can withstand the high temperatures resulting from use of instrument 10. The entire mesh and ring of active electrodes 22 serves as the energy application surface and is powered by the power supply so that the electrosurgical application, such as ablation, occurs over the electrode. Thus, the active aspiration is approximately co-extensive with energy application surface 20. The preferred range of mesh sizes is from approximately 30 mesh to approximately 55 mesh.

The interstices between the mesh permit fluid communication therethrough such that unwanted matter (e.g., ablated tissue, smoke, air bubbles, and other elements or biological debris) may pass through the mesh and into aspiration lumen 50 for transport away form the treatment area. Moreover, because power is supplied substantially uniformly over the entire mesh of active electrode 22, unwanted matter that is too large to fit through the interstices of the mesh are caught on the mesh and accordingly ablated thereby when power is applied to the electroconductive mesh. As the mesh heats up, the matter is ablated until it becomes small enough to fit through the mesh. It will be appreciated that the energy application surface has a uniform electrical potential being one piece across the surface of the mesh. Additionally, a blockage occurring at one portion of the mesh causes an increase in the suction force at unblocked portions of the mesh forming a non-uniform suction path. As the suction force increases in the unblocked areas, a differential axial suction force is created in which the blockage is turned and twisted to continue ablation and pass through apertures 25 to be aspirated through aspiration lumen 50. Thus, active electrode 22 not only provides treatment energy but also permits aspiration therethrough, as well as destruction of larger pieces of unwanted matter during aspiration which might otherwise clog the aspiration lumen 50.

Moreover, in the present embodiment, return electrode 24 is located on shaft 27 proximal to active electrode 22. This defines a unipolar configuration where the return electrode 24 has a larger surface area than active electrode 22 functions as an indifferent return to the power source and the energy is diffuse around electrode 24. This provides the active electrode 22 with a higher current density such that treatment energy is crowded and the treatment effect is generally in the area of tissue in proximity to active electrode 22. In an alternative embodiment, however, return electrode 24 may be located on a surface on the patient's body in the form of a grounding plate or pad. In this configuration, the return electrode functions to return the treatment energy to the power source to define a monopolar configuration.

Referring to FIG. 3, the electrosurgical probe of FIGS. 1 and 2 is illustrated in an end view. Mesh 22A of active electrode 22 forms the energy application surface. The spacing between the mesh form multiple apertures 25 to allows for suction of unwanted matter through the distal end and aspiration opening. Although a substantially flat piece of mesh may be used, the mesh may be formed into any desired shape to vary the contour of the contact surface provided by the mesh. For instance, the mesh forming active electrode 22 may be domed to conform substantially with concave body parts to be treated by electrosurgical aspiration instrument 10. Pointed, convex, rippled, or other contours may be provided instead, depending on user preferences or other contours of the area to be treated. Insulator 28 electrically isolates active electrode 22 from return electrode 24.

In FIG. 4, instead of providing active electrode 22 in the form of a mesh, active electrode 22 may take on an alternative form with apertures provided to permit aspiration therethrough. For example, active electrode 22 may be in the form of a disc or conductive plate 42 with perforations 45 formed therethrough. In an exemplary embodiment, such a plate may be secured within the distal end of annular insulator 28 in place of mesh electrode 22 as shown in FIG. 2. In a preferred embodiment, perforations 45 have a diameter of approximately 0.010–0.020 inches. In general, the perforations should be small enough to reduce particle size passing therethrough such that downstream clogging is minimized while large enough to provide effective aspiration without blockage of the distal tip 12. Likewise, any other type of conductive element formed as a honeycomb or other such shape that permits aspiration therethrough may be used.

Alternative configurations of electrodes which define an energy application surface and permit aspiration therethrough are illustrated in FIGS. 5–7, as described below. It will be appreciated that the form of the active electrode may be modified as desired so long as external access to the internal lumen through the shaft of the electrosurgical aspiration instrument of the present invention is permitted. It will further be appreciated that the form and relative arrangement of the active electrode with respect to the return electrode may be modified as desired. However, it is desirable that the resulting energy application surface extends at least over a portion of the lumen opening to permit cooperation between the energy application surface and the process of aspiration. This provides for reduction in blockage.

Electrosurgical instrument 510 of FIG. 5 has a substantially centrally located electrode 522 and a ring-shaped electrode 524 both of which are positioned at distal end 512 of instrument 510. One of electrodes 522, 524 is an active electrode and the other of electrodes 522, 524 is a return electrode. Both electrodes are supported and electrically isolated by insulator 528. A suitable insulative coating or covering 534 is provided over the exterior surface of instrument 510. Apertures 525 permit aspiration as a suction force is applied to aspiration lumen 550 to draw unwanted matter through apertures and through the instrument 510.

As shown in FIG. 5, insulator 528 has a convex working surface such that central electrode 522 is slightly distal of ring-shaped electrode 524 to form a unipolar configuration. However, it will be appreciated that a substantially flat working surface my be used instead such that the energy application ends of both electrodes are coplanar.

Alternatively, a concave working surface may be used, as in electrosurgical instrument 610 of FIG. 6, such that ring-shaped electrode 624 is slightly distal of central electrode 622. The instrument 610 as shown in FIG. 6 includes apertures 625 within insulator 628 for aspiration from the distal tip 612 through aspiration lumen 650. Outer insulation 634 covers the instrument shaft.

The arrangement and electrical connections of electrodes 522 and 524 of electrosurgical instrument 510 may be appreciated with reference to FIG. 7. It will be understood that a similar arrangement may be used for electrosurgical instruments 510 and 610 as well. In the exemplary embodiment, FIG. 7 illustrates a cross-section through shaft 727 showing electrical power conductor 716, in the form of a wire extending proximally from a power source (not shown) located at proximal end 714 to distal 712 of instrument 710. Power conductor 716 passes through lumen 750 and provides power to central electrode 722. Electrical power conductor 736 is in the form of shaft 727 being electrically conductive and conductor 736 electrically coupled to return electrode 724 via extension 736. Electrical conductors 716, 726, and 736 are electrically isolated from each other in any desired manner, such as in with insulative material such as interior insulation 730 in a manner described above. An insulative coating or covering 734 is provided on the exterior surface of instrument 710, preferably to protect the patient from any energy discharge conducted through electrical conductor 736.

Apertures 525, 625, and 725 are provided through insulator 528, 628 or 728, respectively, such that instruments 510, 610, and 710 also perform an aspiration function as previously described. In particular, the apertures provide for aspiration through the energy application surface which is defined by the electrode planes. It will also be appreciated that certain advantages in localized energy application may be realized due to the placement of both electrodes on the distal tip of the device.

It should be appreciated that active electrode in FIGS. 5–7 can be sized appropriately, relative to return electrode or vice versa, such that application of power to the active electrode and use of the electrosurgical instrument approximates the effect delivered by a bipolar electrosurgical instrument. In a typical bipolar instrument, both electrodes are of the same size and approximately located with in the same proximity such that both electrodes equally affect the tissue area to which the instrument is applied. By sizing the active electrode and the return electrode to be of approximately equivalent sizes, a bipolar effect may be achieved with the present invention. It should further be appreciated that it is possible to size the electrodes in any of the embodiments of the present invention so as to achieve a bipolar effect. The return electrode of the present invention may also be located on the patient's body as discussed above.

FIGS. 8A and 8B, FIGS. 9A and 9B and FIGS. 10A and 10B, illustrate similar embodiments of the electrosurgical aspiration instrument of the present invention. For the sake of simplicity, descriptions of elements or features of the embodiments of FIGS. 8–10 that are substantially the same (and thus referenced by the same reference numbers) are not repeated in detail, reference being made to the description provided in connection with similar elements described with reference to FIGS. 8–10.

FIGS. 8A and 8B illustrate one alternative embodiment of electrosurgical instrument 810 having an active electrode 822 in the form of a ringed coil on distal tip 812. The coil of active electrode 822 may be preformed memory metal or a continuous wire which is looped on distal tip 812.

FIG. 8A is a cross-sectional view showing coil active electrode 822 on distal end 812. The outermost portion of coil active electrode 822 defines energy application surface 820 which forms both an energy treatment surface through the delivery of energy and a mechanical grating surface. Electrode 822 is preferably electrically connected through shaft 827 to the power source through conductor 816. Electrode 822 is in the form of a ring on the distal tip and defines aspiration aperture 825. Insulative material 830 lines aspiration lumen 850 to provide both electrical insulation from any stray electrical current and thermal insulation of the shaft. Return electrode 824 is located internally within aspiration lumen 850 and is electrically isolated from the active electrode 822 by insulator 828 and insulation material 830. Return conductor 826 connects the return electrode 824 to the power source (not shown) at proximal end 814.

In this configuration, the internal return electrode 824 forms a small boiling chamber whereby any matter being aspirated through aperture 825 and past active electrode 822 increases the impedance to increase the delivery of energy in the region between the electrodes. As the energy output from the power source increases in response to the change in impedance, any matter located between the electrodes is ablated to prevent blockage of the aperture 825 and facilitate aspiration through aspiration lumen 850. As smaller matter and debris and any excess fluid pass freely through aperture 825 and between the electrodes, the flow of material cools both electrodes to prevent any hot spots or unwanted ablative treatment effect.

Further, the internal return electrode 824 may provide a benefit of localized heating within the distal end 812 of the surgical instrument 810. As the suction force is applied through aspiration lumen 850 and fluid and surgical by-products flow through aperture 825, a pulling force is created within the local environment surrounding the distal end 812 and active electrode 822. Similar to the blockage and cooling described above, the high intensity energy delivery is limited to an area in close proximity to the aperture 825. Thus, ablation and other surgical procedures can be more precise since energy delivery is limited to the area immediately surrounding aperture 825. The surgeon can control the treatment by direct placement of distal end 812 and electrode 822 on the biological tissue and limit the ablative effect to the tissue.

FIGS. 9A and 9B illustrate another alternative embodiment of electrosurgical instrument 810 having an active electrode 922 in the form of a ring electrode on distal tip 812. The ring electrode configuration of active electrode 922 may be preformed memory metal or a solid metal tip on distal tip 812. Electrode 922 is formed of any biocompatible material including stainless steel, tungsten, titanium or any of its respective alloys.

FIG. 9A is a cross-sectional view showing ring active electrode 922 on distal tip 812. The outermost portion of the ring active electrode 922 defines energy application surface 820 which forms both an energy treatment surface through the delivery of energy and a mechanical smoothing surface. In this embodiment, the rounded surface provides a more diffuse energy application surface than electrode 822 of FIG. 8. This provides a surgeon with the ability to sculpt the body tissue by smoothing irregular areas by passing the curved electrode 922 over the tissue. The electrode 922 may also be formed into a sharp edge to provide a mechanical scraping surface for the removal of unwanted tissue. The electrical current is then crowded for maximum ablative effect along the sharp edge. Electrode 922 is preferably electrically connected through shaft 827 to the power source through conductor 816. Electrode 922 is in the form of a ring on the distal tip and defines aspiration aperture 825. Insulative material 830 lines aspiration lumen 850 to provide both electrical insulation from any stray electrical current and thermal insulation of the shaft. Return electrode 824 is located internally within aspiration lumen 850 and is electrically isolated from the active electrode 922 by insulator 828 and insulation material 830. Return conductor 826 connects the return electrode 824 to the power source (not shown) at proximal end 814.

FIG. 9B is an end view of the distal tip of the instrument of FIG. 9A. Active electrode 922 is shown as a ring around the aspiration lumen to define aperture 825. Return electrode 824 is shown within the aspiration lumen and is electrically isolated from the active electrode 922 by insulator 828. Internal return electrode 824 functions to form a boiling chamber as described above.

FIGS. 10A and 10B illustrate another alternative embodiment of electrosurgical instrument 810 having an active electrode 1022 in the form of a double prong on distal tip 812. The double prong configuration of active electrode 1022 may be preformed memory metal or a solid metal partial loop or coil on distal tip 812. Electrode 1022 is formed of any biocompatible material including stainless steel, tungsten, titanium or any of its respective alloys.

FIG. 10A is a cross-sectional view showing prong active electrode 1022 within insulator 828. The prong is preferably fixed within insulator 828 such that one end is fixed within the insulator 828 and a portion of the prong passes over aperture 825 to fix into the opposite side of the insulator 828. The outermost edge portion of the prong active electrode 1022 defines energy application surface 820 which forms both an energy treatment surface through the delivery of energy and a mechanical treatment surface. In this embodiment, a rounded prong surface provides a smoothing function as described above. The prong active electrode 1022 may also be formed into a sharp edge to provide a mechanical scraping surface for the removal of unwanted tissue. The electrical current is then crowded for maximum ablative effect along the sharp edge. Electrode 1022 is preferably electrically connected through shaft 827 to the power source through conductor 816. Insulative material 830 lines aspiration lumen 850 to provide both electrical insulation from any stray electrical current and thermal insulation of the shaft. Return electrode 824 is located internally within aspiration lumen 850 and is electrically isolated from the active electrode 1022 by insulator 828 and insulation material 830. Return conductor 826 connects the return electrode 824 to the power source (not shown) at proximal end 814.

FIG. 10B is an end view of the distal tip of the instrument of FIG. 10A. Active electrode 1022 is shown as a prong passing over aperture 825. In this embodiment, two prongs pass over the aperture 825 to prevent blockage of the aperture. Both electrode prongs are electrically connected to the power source through a single conductor 816 such that equal power is transmitted to active electrode 822 at the same time for equal effect. It will be appreciated that any number of prongs and the configurations may be use. Return electrode 824 is shown within the aspiration lumen and is electrically isolated from the active electrode 922 by insulator 828.

FIGS. 11A–C illustrate yet another embodiment of the present invention in which the active electrode 1122 is formed from a portion of shaft 1127. FIG. 11A shows a distal end 1112 with active electrode 1122 forming an energy application surface 1120 for treatment of body tissue at a surgical site. At proximal end 1114, conductor 1116 connects the shaft to electrically activate the active electrode 1122. Return electrode 1124 is located externally to shaft 1127 and is electrically isolated from the active electrode 1122 by insulator 1128. Preferably, return electrode 1124 is in the form of a ring electrode around a circumference of the shaft 1127. Return conductor 1126 connects return electrode 1124 to the power source. The return electrical path may also be located on the patient's body as discussed previously. Shaft insulation 1134 covers shaft 1127. The interior suction lumen 1150 may also be lined with an insulative material.

An alternate embodiment of the active as shown in FIG. 11B is similar to the electrosurgical aspiration instrument of FIG. 11A where like elements are described with the same reference numbers. In this configuration, active electrode 1122 has cutouts 1129 to form a grating surface with cutout edges 1180. By configuring the active electrode with cutout edges, the active electrode 1122 forms high current densities at the energy application surface 1120 such that current is crowded at the edges 1180. Thus, maximum ablation in combination with a mechanical cutting and grating effect is achieved. Additionally, fluid may be delivered through the lumen to be delivered to the site when connected to a fluid delivery source and aspirated through the same lumen 1150 when connected to a suction source.

FIG. 11C illustrates a perspective view of the electrosurgical instrument of FIG. 11B. Edges 1180 protrude beyond the shaft and insulator 1128 for both delivery of treatment energy for ablation, cutting or coagulation and mechanical scraping for removal of unwanted tissue. As the current is crowded at the edges 1180, the mechanical scraping and cutting is facilitated by providing an ablative effect at a precise cutting point along the tissue. In this embodiment, the treated tissue is then aspirated through the aspiration lumen away from the surgical site.

FIGS. 12A and 12B illustrate another embodiment of the present invention in which the active electrode is formed into a cross-shape with aspiration provided through and around the arm extensions. FIG. 12A shows a cross-section view of the active electrode 1222 of electrosurgical instrument 1210. The active electrode 1222 is located at the distal end 1212 of shaft 1227 of instrument 1210. Shaft 1227 may be covered by shaft insulation 1234. Active electrode 1222 is connected to a power source (not shown) by electrical conductor 1216. The arm extensions of active electrode 1222 are mostly planar with the main body of the electrode and extend outward to form edges 1280. Apertures 1225 are formed between the arms of active electrode 1222. A middle portion of active electrode 1222 may also be raised from the main body to form a middle edge 1280. By raising edges 1280, the current is crowded along the edges for increased electrical density at edges 1280 for an ablative effect. Edges 1280 may also be configured and sharpened for a simultaneous mechanical scraping and grating effect at the surgical site.

The placement of edges 1280 also prevents blockage of the apertures 1225 as current is delivered to the active electrode. As the current is crowded along edges 1280, any matter resulting from the surgical site which is blocking the aperture 1225 increases the impedance between edges 1280 causing an increase in power. As the power increases, the treatment energy ablates the unwanted matter into a smaller size to pass through the aperture. For example, if unwanted matter blocks one quadrant of the aperture 1225, impedance is increased along edge 1280 near the blockage. Since the force of suction is equal through the apertures, the suction unequally increases at the other quadrants thereby pulling the blockage along various axial planes. The increased treatment energy delivery ablates portions of the blockage to a point in which the unwanted matter moves easily through any of the apertures. This effect is similar to the mesh configuration of FIG. 1 in which the ablative effect due to the electrode design across the aspiration aperture opening assists in further ablation of any blockage or unwanted material. The differential suction over the other non-blocked apertures creates a differential axial aspiration effect thereby assisting in removing the blockage.

Return electrode 1224 is located internally within aspiration lumen 1250 to form a boiling chamber as described above. The electrical energy is returned to the power source from return electrode 1224 by return conductor 1226. The return electrode 1224 is electrically insolated from active electrode 1222 by insulator 1228.

FIG. 12B is a perspective view of the instrument 1212 of FIG. 12A. In this embodiment, edges 1280 are raised to form a cup or pocket for ablation. Edges 1280 function as both a mechanical cutting surface edge and a current crowding edge for effective ablation.

Another embodiment is illustrated by FIG. 13A in which electrosurgical instrument 1310 has an ashtray configuration of the active electrode 1322. Active electrode 1322 is located on the distal end 1312 of shaft 1327. The instrument shaft may be covered with shaft insulator 1334. Active electrode 1322 is in an ashtray configuration where cutouts 1329 are formed in energy application surface 1320. By forming cutouts 1329, edges 1380 are formed within the energy application surface 1320 of active electrode 1322. Edges 1380 form both a mechanical tissue removal surface simultaneously with a current crowding edge for maximum energy delivery effect. Blockage of aperture 1325 can also be prevented and eliminated by configuring active electrode 1322 with edges 1380 near the aperture 1325. Electrical conductor 1316 electrically couples the electrode 1322 to the power source (not shown). Active electrode 1322 is configured with a central aperture 1325 which communicates with aspiration lumen 1350. Return electrode 1324 is located within aspiration lumen 1350 and is proximal to active electrode 1322 to form a boiling chamber as described above. Insulator 1328 insulates electrodes 1322 and 1324. An internal lining 1330 may also line aspiration lumen 1350 to function as both an electrical and thermal insulator.

FIG. 13B is a perspective view of FIG. 13A in which the active electrode 1322 is show in the ashtray configuration. Cutouts 1329 within the electrode define edges 1380 for the mechanical and electrical effect as described above. Aperture 1325 communicates through instrument 1310 with aspiration lumen 1350.

FIG. 14A and 14B illustrate cross-sectional and perspective views of an alternative embodiment of the electrosurgical aspiration instrument 1310 as described FIGS. 13A and 13B. Similar elements will be referenced to FIGS. 13A and 13B. In this embodiment, return electrode 1424 is located external along the shaft 1327. Return electrode 1426 electrically completes the current path to the power source from the active electrode 1322. The return electrode 1424 is preferably a ring electrode located on the surface of shaft 1327 and is isolated from the active electrode 1322 by insulator 1328.

FIGS. 15A–C illustrate different views of ashtray electrode according to one alternative embodiment of the active electrode as described above. Like elements will be referenced by the same reference numbers. FIG. 15A shows a close-up perspective view of active electrode 1522 in which at least one aperture 1525 is provided through active electrode 1522. Active electrode 1522 is configured to crowd the current creating a high current density along a circumferential edge 1580. Edge 1580 defines energy application surface 1520. Cutouts 1529 form a pattern along edge 1580 to maximize the current crowding. As the current is crowded along edges 1580, a mechanical scraping and ablative effect occurs simultaneously. Current is also crowded edge 1580 formed within aperture 1525 to prevent blockage of the aperture. As energy is applied to the active electrode, the sharp edge of surface 1580 provides both a surface for the delivery of RF power for ablation while simultaneously providing a mechanical grating or scraping surface for scraping tissue at the surgical tissue site. It will be appreciated that edge 1580 of electrode 1520 may be rounded such that a smoothing surface may be formed and sculpting may be performed with the instrument of the present invention.

As by-products of ablation and/or coagulation are created at the surgical site, negative pressure created by suction through the lumen and electrosurgical instrument aspirates the additional matter through aperture 1525. However, blockage and clogging of the aperture 1525 may undesirably increase the ablation effect by reducing the flow of liquid and tissue through aperture 1525. By-products of surgery such as biological tissue debris could result from the ablation and cutting process. As this matter becomes dislodged and freely movable within the surgical site, the biological tissue may completely block any and all apertures into the instrument. Thus, the cooling effect due to the flow of matter and liquid is reduced thereby increasing the delivery of treatment energy to the site possibly causing unnecessary ablation and injury to the patient.

To combat blockage and potential injury, edges 1580 may be configured with reference to FIG. 12 wherein a portion of edges 1580 is configured and positioned near or within aperture 1525. As the impedance increases due to blocked tissue within aperture 1525, the tissue is further treated with energy at edges 1580 whereby the tissue is further ablated to a size to fit through aperture 1525. The irregular shape of aperture 1525 in combination with edges 1580 provides for non-uniform and non-round apertures such that both an electrical and mechanical effect combine to prevent blockage within the opening thereby increasing the efficiency of the electrosurgical instrument 1510.

FIG. 15B shows an end view of the distal electrode tip 1512. Energy application surface 1520 and edge 1580 are shown with cutouts 1529. It will also be appreciated that the number, sizes and placement of cutouts 1529 within surface 1520 may vary to provide different ablation effects and patterns. The electrical current is crowded and has the greatest density at surface 1520 and edge 1580 such that ablation, cutting and/or coagulation occurs along edge 1580.

FIG. 15C is a cross-sectional view of the distal tip of FIG. 15B in which the active electrode 1522 on distal end 1512 is shown along Line A—A. The energy application surface 1520 is shown in detail as a sharp edge 1580 with both an electrical effect for ablation and mechanical effect for scraping. Edge 1580 is shown to be intruding into a portion of aperture 1525 which leads to aspiration lumen 1550. With reference to FIG. 12 above, the effect of suction through a non-uniform configuration of aperture 1525 prevents the blockage and clogging of the aspiration opening such that the negative pressure pulls the blockage into the lumen across different axial planes. For example, as an unwanted by-product matter hits aperture 1525, it lodges on a portion of edge 1580. As the suction is applied to the lumen and through the opening, a portion of the matter is pulled on the portions away from the lodged portion along edge 1580. This allows the matter to twist and turn in different axial planes whereby the unwanted matter moves and has a different and more compatible physical orientation to move through aperture 1525.

FIGS. 16A and B illustrate a further alternative embodiment of the present invention in which the active and return electrodes 1622, 1624 lie in substantially the same plane of the energy application surface 1620 at the distal end 1612 of instrument 1610 to define a true bipolar configuration. Such position of electrodes 1622 and 1624 may be accomplished by forming each electrode as an arcuate element positioned on the distal end 1612 of instrument 1610. Electrodes 1622 and 1624 are supported by insulator 1628 which serves the additional function of electrically isolating electrodes 1622 and 1624. Cutouts 1629 are formed in insulator 1628 to space apart and thus further electrically isolate electrodes 1622 and 1624. Central opening 1625 allows for aspiration.

Electrodes 1622 and 1624 are separately coupled to the power source by separate respective conductive elements 1616 and 1626. Conductive elements preferably extend from distal end 1612 to proximal end 1614 of instrument 1610 through lumen 1650. Although conductive elements 1616 and 1626 extend through the central opening 1625 through insulator 1628 to be coupled with electrodes 1622 and 1624 on the distal-most end of insulator 1628, it will be appreciated that other arrangements are also within the scope of the present invention. For instance, conductive elements 1616 and 1626 may extend through a passage formed through insulator 1628 to communicate lumen 1650 with electrodes 1622, 1624. Lumen 1650 may be used for aspiration as previously described.

It will be appreciated that the above-described arrangements that provide an energy application surface area at the distal tip of the electrosurgical instrument may be applied to an instrument that is not capable of aspiration. Thus, insulator 1628 of instrument 1610 may be a substantially solid element with passages therethrough for the purpose of electrically coupling electrodes 1622 and 1624 to the power source but not for aspiration purposes. The arrangement of the active and return electrodes may be further modified as in FIGS. 10 and 11 to provide and energy application surface area that, although contoured (i.e., not completely planar), still remains at the distal end of the instrument, substantially transverse to the longitudinal axis, without extending along a distal portion of the side walls of the instrument (such as in instrument 10 of FIGS. 1 and 2).

FIGS. 17A and 17B illustrate another embodiment of the electrosurgical aspiration instrument 1710 of the present invention in which the active electrode 1722 and the return electrode 1724 are comparably sized and located in close proximity to each other at the distal end 1712. This arrangement of electrodes 1722 and 1724 define a true bipolar configuration. Active electrode 1722 is a single disc shaped electrode which is centrally located at distal end 1712 within insulator 1728. Return electrode 1724 is a ring electrode located substantially along the same plane at the circumferential edge of insulator 1728. The effective area size of both electrodes are similar such that the delivered treatment energy is equal between both electrodes. Apertures 1725 are located within insulator 1828 and communicates with aspiration lumen 1750. As the ablation, cutting and coagulation occur at the active electrode 1722, the suction applied to the aspiration lumen forces the by-products and excess fluid through apertures 1725.

FIG. 17B shows a cross-sectional view in which the active electrode 1722 is coupled to a power supply (not shown) at the proximal end 1714 by power conductor 1716. Return electrode 1724 is coupled to electrically conductive shaft 1727 by extension 1736 to complete the circuit to the power supply. Shaft 1727 is covered by shaft insulation 1734.

FIGS. 18A–C illustrate a further alternative embodiment of the electrosurgical aspiration instrument 1810 of the present invention in which the active and return electrodes 1822, 1824 lie in the same plane at the distal end 1812. The active and return electrodes are substantially configured similarly such that the two conductors 1816 and 1826 are electrically coupled through shaft 1827 to the distal end 1812. Electrodes 1822 and 1834 are electrically isolated by insulator 1828. Delivery of energy is equal to both electrodes such that an equal, bipolar effect occurs at the surgical site. Both electrodes extend from one side of aspiration aperture 1825 to a point across the aperture and return to the generator. One electrode serves as an active electrode and one electrode serves as a return electrode. It will be appreciated that either electrode may be an active or a return since the polarity of the power generator may be reversed. Because both electrodes are configured across the aspiration aperture 1825, clogging and blockage of the aperture is prevented or reduced.

FIG. 19 illustrates a perspective view of an electrosurgical aspiration instrument 1910 according to the present invention. Aspiration line 1952 is attached to proximal handle 1917. Aspiration line 1952 connects to a suction device and receptacle (not shown) which provides a negative pressure through the instrument in order to aspirate ablation by-products through distal tip 1912 through probe shaft 1927. A power receptacle 1914 connects instrument 1910 to a power source (not shown). An actuator 1918 controls the amount and force of suction through the aspiration line 1952 and is controlled by a roller. Vacuum line connector 1957 connects to the aspiration receptacle. It will be appreciated that any device or mechanism to control the amount and force of suction may be used to aspirate surgical material through the instrument 1910.

FIGS. 20 and 21 show two alternative embodiments of the distal end 1912 of FIG. 19 of the present invention in which the shaft 1927 of distal end 1912 is pre-bent. As discussed above, it is preferable that the shaft 1927 is not flexible such that the aspiration lumen is not pinched nor crimped thereby blocking suction. The reduction of the suction force as discussed above may lead to an increase in the ablation effect. FIG. 20 shows a 30 degree bend in distal end 1912 and FIG. 21 is a 90 degree bend. While the degree of pre-bent angle is not limited to these specific degrees, it will be appreciated that the manufacture of the pre-bent distal end 1912 be optimized for access to a particular body position or part for a desired surgical procedure and corresponding ablation effect. For example, the 90 degree bend in distal end 1912 as shown in FIG. 21 allows access to areas such as the subacromial space under the acromium in the shoulder. This allows for better access by a surgeon to the particular body part.

The embodiments of the electrosurgical instrument of the present invention that permit an aspiration function in combination with an electrosurgical function are particularly useful for surgical procedures requiring ablation of tissue or other body parts. In order to perform an ablation function, the energy supplied to the electrosurgical aspiration instrument should be in the range of 100–500 KHz. This range may be varied depending on the materials used to form the instrument as well as depending on the particular application of the instrument in the surgical procedure. The lowest frequency used typically is selected such that use of the instrument does not interfere with other tissue nor stimulate nerves in the area, etc. Thus, isolated treatment of the selected tissue area is permitted. The highest frequency used typically is limited depending on the desired results that would be achieved by such frequency. For instance, at too high a frequency, appropriate ablation may not be achievable and blockage of the lumen by debris may occur.

Power may be provided by commercially available RF energy sources. Such RF energy sources may include generators which control the temperature of the electrosurgical instrument. Power may also be regulated by feedback to prevent overpower and undesired ablation or coagulation as such.

As mentioned above, the electrosurgical instrument of the present invention may be used for any of a variety of applications and procedures, depending on the nature of the energy supplied thereto by the power source. It will, therefore, be appreciated that the energy supplied to the electrosurgical instrument of the present invention may be varied depending on the application desired. The energy level may even be varied during use to perform a variety of functions, such as ablation followed or accompanied by cauterization or coagulation as necessary.

While the foregoing description and drawings represent the preferred embodiments of the present invention, it will be understood that various additions, modifications and substitutions may be made therein without departing from the spirit and scope of the present invention as defined in the accompanying claims. In particular, it will be clear of those skilled in the art that the present invention may be embodied in other specific forms, structures, arrangements, proportions, and with other elements materials, and components, without departing from the spirit or essential characteristics thereof. The presently disclosed embodiments are, therefore, to be considered in all respects as illustrative and not restrictive, the scope of the invention being indicated by the appended claims and not limited to the foregoing descriptions.

What is claimed is:

1. A surgical instrument, comprising;
   a shaft having distal and proximal ends, said shaft defining an aspiration lumen having a diameter;
   a conductive member disposed at said distal end of said shaft across said aspiration lumen and forming an active electrode, said conductive member having at least one opening therethrough communicating with the aspiration lumen such that material may be aspirated through said active electrode, said at least one opening being individually smaller than said lumen diameter to avoid clogging of aspirated material downstream of said at least one opening, said conductive member having an ashtray shape;
   a first conductor connected to said conductive member;
   a return electrode disposed around said shaft proximally from said active electrode; and
   a second conductor connected to said return electrode.

2. The surgical instrument of claim 1 wherein said active electrode further comprises a sharp edge forming a mechanical treatment surface.

3. The surgical instrument of claim 1 wherein said active electrode includes a mechanical treatment surface having an edge configured to form a high current density at said edge for maximum ablative effect along said edge.

4. A surgical instrument for use with a power source, comprising:
   a shaft having distal and proximal ends, said shaft defining an aspiration lumen having a diameter and having an opening at said distal end;
   a conductive member disposed at said distal end of said shaft across said aspiration lumen to define an energy application plane across said lumen opening and forming an active electrode, said conductive member having at least one opening therethrough communicating with the aspiration lumen such that material may be aspirated through said active electrode across said energy application plane, said at least one opening being individually smaller than said lumen diameter to avoid clogging of aspirated material downstream of said at least one opening, said active electrode having an ashtray shape and having a mechanical treatment surface for the mechanical removal of tissue at a surgical site;
   a first conductor adapted for coupling to the power source and connected to said conductive member;
   a return electrode disposed around said shaft proximally from said active electrode; and
   a second conductor connected to said return electrode.

5. The surgical instrument of claim 4, wherein one of said first and second conductors is formed by said shaft.

6. The surgical instrument of claim 4, wherein said lumen has an insulative coating.

7. The surgical instrument of claim 4, further comprising a suction source coupled to the proximal end of the shaft for providing negative pressure to said aspiration lumen so as to cause matter to be aspirated through said at least one opening of said conductive member.

8. The surgical instrument of claim 4, wherein said mechanical treatment surface is an edge provided on said active electrode with a high current density to provide an electrical and mechanical effect.

9. The surgical instrument of claim 4, wherein said active electrode includes a sharp edge which defines said mechanical treatment surface.

10. The surgical instrument of claim 4, wherein said active electrode is concentrically disposed at said distal end of said shaft.

11. The surgical instrument of claim 4, wherein the proximal end of said shaft is mounted to a handle, said handle providing at least one connection for at least said first conductor to a power supply and a connection for said aspiration lumen to a vacuum source.

* * * * *